US007799826B2

(12) United States Patent
Smith et al.

(10) Patent No.: US 7,799,826 B2
(45) Date of Patent: Sep. 21, 2010

(54) INHIBITION OF FATTY ACID SYNTHASE BY BETA-LACTONES AND OTHER COMPOUNDS FOR INHIBITION OF CELLULAR PROLIFERATION

(75) Inventors: Jeffrey W. Smith, San Diego, CA (US); Fumiko Axelrod, San Diego, CA (US); Steven J. Kridel, Clemmons, NC (US)

(73) Assignee: Burnham Institute for Medical Research, La Jolla, CA (US)

( * ) Notice: Subject to any disclaimer, the term of this patent is extended or adjusted under 35 U.S.C. 154(b) by 923 days.

(21) Appl. No.: 10/418,513

(22) Filed: Apr. 16, 2003

(65) Prior Publication Data

US 2004/0024050 A1 Feb. 5, 2004

Related U.S. Application Data

(60) Provisional application No. 60/373,181, filed on Apr. 17, 2002.

(51) Int. Cl.
*A61K 31/335* (2006.01)
(52) U.S. Cl. ...................... 514/449; 435/375
(58) Field of Classification Search .............. 436/93, 436/128; 514/449; 435/375
See application file for complete search history.

(56) References Cited

U.S. PATENT DOCUMENTS

| | | | | |
|---|---|---|---|---|
| 4,598,089 | A | 7/1986 | Hadvary et al. | 514/449 |
| 4,806,564 | A | 2/1989 | Chabala et al. | 514/449 |
| 4,873,260 | A | 10/1989 | Alberts et al. | 514/449 |
| 4,931,463 | A | 6/1990 | Barbier et al. | 514/422 |
| 4,983,746 | A | 1/1991 | Barbier et al. | 549/328 |
| 5,175,186 | A | 12/1992 | Barbier et al. | 514/449 |
| 5,246,960 | A | 9/1993 | Barbier et al. | 514/422 |
| 5,260,310 | A | 11/1993 | Derungs et al. | 514/449 |
| 5,376,674 | A | 12/1994 | Derungs et al. | 514/422 |
| 5,399,720 | A | 3/1995 | Karpf et al. | 549/292 |
| 5,466,708 | A | 11/1995 | Derungs et al. | 514/449 |
| 5,759,837 | A | 6/1998 | Kuhajda et al. | 435/193 |

FOREIGN PATENT DOCUMENTS

| | | | |
|---|---|---|---|
| EP | 0185359 A2 | | 12/1985 |
| JP | 3115274 | | 5/1991 |
| WO | WO 00/04300 | | 1/2000 |
| WO | 02/24674 A1 | * | 3/2002 |

OTHER PUBLICATIONS

Sausville et al. Cancer Research, 2006, vol. 66, pp. 3351-3354.*
Johnson et al. British J. of Cancer, 2001, 84(10):1424-1431.*
Alo et al., "Expression of Fatty Acid Synthase (FAS) as a Predictor of Recurrence in Stage I Breast Carcinoma Patients," *Cancer* 77:474-482 (1996).
Auerbach and Auerbach, "Angiogenesis Inhibition: A Review," *Pharmac. Ther.* 63:265-311 (1994).
Creamer and Barker, "Vascular proliferation and angiogenic factors in psoriasis," *Clin. Exp. Dermatol.* 20:6-9 (1995).
De Vos et al., "Cellular pharmacology of cerulenin analogs that inhibit protein palmitoylation," *Biochem. Pharmacol.* 62:985-995 (2001).
Folkman, "Angiogenesis in cancer, vascular, rheumatoid and other disease," *Nat. Med.* 1(1):27-31 (1995).
Greenbaum et al., "Epoxide electrophiles as activity-dependent cysteine protease profiling and discovery tools," *Chem. Biol.* 7:569-581 (Aug. 1, 2000).
Hadvary et al., "The Lipase Inhibitor Tetrahydrolipstatin Binds Covalently to the Putative Active Site Serine of Pancreatic Lipase," *J. Biol. Chem.* 266(4):2021-2027 (Feb. 5, 1991).
Jochen et al., "Inhibitory effects of cerulenin on protein palmitoylation and insulin internalization in rat adipocytes," *Biochim. Biophys. Acta.* 1259:65-72 (1995).
Kidd et al., "Profiling Serine Hydrolase Activities in Complex Proteomes," *Biochemistry* 40:4005-4015 (2001).
Kuhajda, "Fatty-Acid Synthase and Human Cancer: New Perspectives on Its Role in Tumor Biology," *Nutrition* 16:202-208 (2000).
Kuhajda et al., "Fatty acid synthesis: A potential selective target for antineoplastic therapy," *Proc. Natl. Acad. Sci. USA* 91:6379-6383 (Jul. 1994).
Kuhajda et al., "Synthesis and antitumor activity of an inhibitor of fatty acid synthase," *Proc. Natl. Acad. Sci. USA* 97:3450-3454 (Mar. 28, 2000).
Lawrence et al., "Structure-Activity Studies of Cerulenin Analogues as Protein Palmitoylation Inhibitors," *J. Med. Chem.* 42:4932-4941 (1999).
Li et al., "Pharmacological Inhibition of Fatty Acid Synthase Activity Produces Both Cystostatic and Cytotoxic Effects Modulated by p53$^1$," *Cancer Res.* 61:1493-1499 (Feb. 15, 2001).
Liu et al., "Activity-based protein profiling: The serine hydrolases," *Proc. Natl. Acad. Sci. USA* 96(26):14694-14699 (Dec. 21, 1999).
McNeely and Benfield, "Orlistat," *Drugs* 56(2):241-249 (Aug. 1998).
Paterson and Hulme, "Total Synthesis of (-)-Ebelactone A and B$^1$," *J. Org. Chem.* 60(11):3288-3300 (1995).

(Continued)

*Primary Examiner*—James D Anderson
(74) *Attorney, Agent, or Firm*—Arnall Golden Gregory LLP; Robert A. Hodges

(57) ABSTRACT

The present invention features methods of treating a cancer in a subject by administering an effective amount of a beta-lactone to the subject. The invention also features methods of inhibiting angiogenesis in a subject by administering an effective amount of an inhibitor of fatty acid synthase to the subject. These methods can be used to treat a variety of cancers and other diseases and conditions. The invention also features methods of identifying beta-lactones and other compounds that can be used in the methods of the invention for the treatment of tumors, inhibition of angiogenesis, and the treatment of diseases and conditions that involve pathological angiogenesis.

6 Claims, 6 Drawing Sheets

OTHER PUBLICATIONS

Patricelli et al., "Direct visualization of serine hydrolase activities in complex proteomes using fluorescent active site-directed probes," *Proteomics* 1:1067-1071 (2001).

Pizer et al., "Fatty Acid Synthase (FAS): A Target for Cytotoxic Antimetabolites in HL60 Promyelocytic Leukemia Cells[1]," *Cancer Res.* 56:745-751 (Feb. 15, 1996).

Pizer et al., "Increased Fatty Acid Synthase as a Therapeutic Target in Androgen-Independent Prostate Cancer Progression," *The Prostate* 47:102-110 (2001).

Pizer et al., "Malonyl-Coenzyme-A Is a Potential Mediator of Cytotoxicity Induced by Fatty-Acid Synthase Inhibition in Human Breast Cancer Cells and Xenografts," *Cancer Res.* 60:213-218 (Jan. 15, 2000).

Pizer et al., "Pharmacological Inhibitors of Mammalian Fatty Acid Synthase Suppress DNA Replication and Induce Apoptosis in Tumor Cell Lines[1]," *Cancer Res.* 58:4611-4615 (Oct. 15, 1998).

Thupari et al., "Fatty Acid Synthase Inhibition in Human Breast Cancer Cells Leads to Malonyl-CoA-Induced Inhibition of Fatty Acid Oxidation and Cytotoxicity," *Biochem. Biophys. Res. Commun.* 285(2):217-223 (2001).

Umezawa et al., "Ebelactone, An Inhibitor of Esterase, Produced By Actinomycetes," *J. Antibiot.* (Tokyo) 33(12):1594-1596 (Dec. 1980).

Uotani et al., "Structural Studies on Ebelactone A and B, Esterase Inhibitors Produced by Actinomycetes," *J. Antibiot.* (Tokyo) 35(11):1495-1499 (Nov. 1982).

* cited by examiner

INHIBITION OF FATTY ACID SYNTHASE BY BETA-LACTONES AND OTHER COMPOUNDS FOR INHIBITION OF CELLULAR PROLIFERATION

CROSS-REFERENCE TO RELATED APPLICATIONS

This application claims benefit of priority from U.S. Provisional Application Serial No. 60/373,181, filed Apr. 17, 2002, which application is hereby incorporated by reference in its entirety.

STATEMENT OF FEDERALLY SPONSORED RESEARCH

This invention was made with government support under Grant Nos. CA 69036 and 5 P01 CA82713-05, both awarded by the National Institutes of Health. The government has certain rights in this invention.

FIELD OF THE INVENTION

This invention relates generally to the treatment of cancer by administration of beta-lactones to inhibit the enzymatic activity of fatty acid synthase. The invention also relates generally to the inhibition of angiogenesis and the treatment of diseases that involve pathological angiogenesis by administration of compounds (e.g., beta-lactones) that inhibit the enzymatic activity of fatty acid synthase.

BACKGROUND OF THE INVENTION

Fatty acid synthase (FAS) is a multifunctional enzyme that catalyzes the synthesis of long-chain fatty acids from small carbon substrates. The enzyme contains six separate enzymatic pockets along with an acyl carrier protein, which act sequentially to perform repeated condensations of acetyl CoA and malonyl CoA, yielding predominantly palmitate, a sixteen-carbon polyunsaturated fatty acid. Following seven such condensation cycles, palmitate remains covalently attached to the acyl carrier protein of the enzyme until it is liberated by the final enzymatic pocket on the enzyme, the intrinsic thioesterase.

Fatty acid synthesis has long been thought unimportant in most normal tissues, and the enzyme is down-regulated by dietary lipid. However, increased FAS expression and activity in tumors is well documented. Tumor cell dependence on de novo fatty acid synthesis is viewed as a metabolic anomaly, with the endogenously-synthesized fatty acids apparently incorporated into membrane phospholipids in preparation for cell division.

Given the prevalence of cancer that is refractory to current therapies, there is a need in the art for new cancer treatment strategies.

SUMMARY OF THE INVENTION

Described herein are two surprising discoveries: first, that beta lactones can be used to inhibit the growth of tumor cells that express fatty acid synthase, and second, that inhibitors of fatty acid synthase activity can be used to inhibit endothelial cell proliferation and angiogenesis.

In a first aspect, the invention features a method of treating or preventing a cancer in a subject, comprising administering an effective amount of a beta-lactone to the subject, thereby treating or preventing the cancer in the subject.

In various embodiments of the first aspect of the invention, the cancer comprises cells that express fatty acid synthase. The cancer can be any cancer that expresses fatty acid synthase, for example, but not limited to, a leukemia, a lymphoma, or a carcinoma (e.g., a carcinoma of the breast, prostate, ovary, endometrium, colon, stomach, liver, pancreas, esophagus, lung, oral mucosa, or skin).

In a second aspect, the invention features a method of inducing apoptosis of a cell that expresses fatty acid synthase in a subject, comprising administering an effective amount of a beta-lactone to the subject, thereby inducing apoptosis of the cell that expresses fatty acid synthase in the subject.

In various embodiments of the second aspect of the invention, the cell can be a tumor cell, for example, but not limited to, a leukemia, lymphoma, or carcinoma cell. In other embodiments of the second aspect of the invention, the cell overexpresses fatty acid synthase. In still other embodiments of the second aspect of the invention, the subject is identified as being in need of administration of a beta-lactone to induce apoptosis of a cell that expresses fatty acid synthase.

In a third aspect, the invention features a method of inducing cell cycle arrest of a cell that expresses fatty acid synthase in a subject, comprising administering an effective amount of a beta-lactone to the subject, thereby inducing cell cycle arrest of the cell that expresses fatty acid synthase in the subject.

In various embodiments of the third aspect of the invention, the cell can be a tumor cell, for example, but not limited to, a leukemia, lymphoma, or carcinoma cell. In other embodiments of the second aspect of the invention, the cell overexpresses fatty acid synthase. In still other embodiments of the second aspect of the invention, the subject is identified as being in need of administration of a beta-lactone to induce cell cycle arrest of a cell that expresses fatty acid synthase.

In a fourth aspect, the invention features a method of treating or preventing a cancer of the intestinal mucosa in a subject, comprising: a) identifying the subject as being in need of treatment with a beta-lactone to treat or prevent the cancer, and b) orally administering an effective amount of the beta-lactone to the subject, thereby treating or preventing the cancer of the intestinal mucosa in the subject.

In a fifth aspect, the invention features a method of inhibiting angiogenesis in a subject, said method comprising administering an effective amount of an antagonist of fatty acid synthase to the subject, thereby inhibiting angiogenesis in the subject.

In various embodiments of the fifth aspect of the invention, the antagonist inhibits activity of the ketoacyl synthase domain of fatty acid synthase. For example, the antagonist can be cerulenin or c75.

In other embodiments of the fifth aspect of the invention, the antagonist inhibits activity of the thioesterase domain of fatty acid synthase. For example, the antagonist can be a beta-lactone, for example, but not limited to, tetrahydrolipstatin, ebelactone A, or ebelactone B, and angiogenesis is inhibited for the purpose of treating or preventing a tumor.

In still other embodiments of the fifth aspect of the invention, angiogenesis is inhibited for the purpose of treating or preventing macular degeneration, diabetic retinopathy, arthritis, obesity, psoriasis, eczema, scleroderma, a haemangioma, an angiosarcoma, or Kaposi's sarcoma.

In a sixth aspect, the invention features a method of identifying a beta-lactone that inhibits tumor cell proliferation, comprising: a) contacting a sample comprising fatty acid synthase with a beta-lactone, and b) measuring fatty acid synthase activity in the sample, whereby a decrease in the amount of fatty acid synthase activity in the sample, relative to the amount of fatty acid synthase activity in a sample not contacted with the beta-lactone, identifies a beta-lactone that inhibits tumor cell proliferation.

In various aspects of the sixth aspect of the invention, the compound induces cell cycle arrest of a tumor cell. In other aspects of the sixth aspect of the invention the compound induces apoptosis of a tumor cell.

In a seventh aspect, the invention features a method of identifying a beta-lactone that inhibits tumor cell proliferation, comprising: a) contacting a sample comprising tumor cells with a beta-lactone, and b) measuring the amount of cell proliferation, cell cycle progression, cell cycle arrest, or apoptosis in the sample exposed to the beta-lactone, whereby a decrease in cell proliferation, a decrease in cell cycle progression, an increase in cell cycle arrest, or an increase in apoptosis in the sample comprising tumor cells exposed to the beta-lactone, relative to the amount of proliferation, cell cycle progression, cell cycle arrest, or apoptosis in a sample comprising tumor cells not contacted with the beta-lactone, identifies a beta-lactone that inhibits proliferation of a tumor cell.

In an eighth aspect, the invention features a method of identifying a compound that inhibits angiogenesis, comprising: a) contacting a sample comprising fatty acid synthase with the compound, and b) measuring fatty acid synthase activity in the sample, whereby a decrease in the amount of fatty acid synthase activity in the sample, relative to the amount of fatty acid synthase activity in a sample not contacted with the compound, identifies a compound that inhibits angiogenesis. For example, the compound can be a beta-lactone.

In a ninth aspect, the invention features a method of identifying a beta-lactone that inhibits angiogenesis, comprising: a) contacting a sample comprising endothelial cells with a beta-lactone, and b) measuring the amount of endothelial cell proliferation, cell cycle progression, or cell cycle arrest in the sample, whereby a decrease in cell proliferation, a decrease in cell cycle progression, or an increase in cell cycle arrest in the sample, relative to the amount of cell proliferation, cell cycle progression, or cell cycle arrest in a sample comprising endothelial cells not contacted with the beta-lactone, identifies a beta-lactone that inhibits angiogenesis.

In a tenth aspect, the invention features a method of identifying a beta-lactone that inhibits angiogenesis, comprising: a) contacting a sample with the beta-lactone, wherein the sample comprises angiogenic cells, and b) measuring the amount of angiogenesis in the sample, whereby a decrease in the amount of angiogenesis in the sample, relative to the amount of angiogenesis in a sample not contacted with the beta-lactone, identifies a beta-lactone that inhibits angiogenesis.

In any of the above aspects of the invention, the beta-lactone can be any beta-lactone (or any combination of beta-lactones), for example, but not limited to, a beta-lactone wherein $R^1$ is a straight-chain alkyl group (e.g., but not limited to, tetrahydrolipstatin, ebelactone A, or ebelactone B).

In any of the above aspects of the invention, the beta lactone can have the formula I:

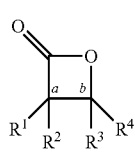

I wherein $R^1$, $R^2$, $R^3$, and $R^4$ are, independently, hydrogen, an alkyl group, a cycloalkyl group, a heterocyloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof, and wherein the stereochemistry at carbons a and b is R or S, as described herein.

For example, in various embodiments of any of the above aspects of the invention, $R^2$ and $R^4$ are hydrogen. Moreover, in various embodiments of any of the above aspects of the invention, $R^1$ is an alkyl group, for example, a straight chain $C_1$ to $C_{20}$ alkyl group. In still other embodiments, $R^3$ is an alkyl group comprising an ester group (for example, a straight chain $C_3$ to $C_{20}$ alkyl group); moreover, the ester group can further comprise an amide group. In yet other embodiments, $R^3$ is an alkenyl group (for example, a straight chain $C_3$ to $C_{20}$ alkenyl group) comprising an ester group; moreover, the ester group can further comprise an amide group.

In still other embodiments of any of the above aspects of the invention, $R^2$ and $R^4$ are hydrogen, the stereochemistry at carbon a is S, and the stereochemistry at carbon b is S; moreover, $R^1$ can be an alkyl group or an alkenyl group. For example, in some embodiments of any of the above aspects of the invention, $R^1$ is an alkyl group, $R^2$ and $R^4$ are hydrogen, $R^3$ is an alkyl group comprising an ester group, the stereochemistry at carbon a is S, and the stereochemistry at carbon b is S. In other embodiments of any of the above aspects of the invention, $R^1$ is an alkyl group, $R^2$ and $R^4$ are hydrogen, $R^3$ is an alkenyl group comprising an ester group, the stereochemistry at carbon a is S, and the stereochemistry at carbon b is S. For example, the compound can be tetrahydrolipstatin or lipstatin.

In yet other embodiments of any of the above aspects of the invention, $R^2$ and $R^4$ are hydrogen, and $R^1$ is a $C_1$ to $C_5$ alkyl group. For example, the alkyl group can be methyl, ethyl, propyl, isopropyl, butyl, isobutyl, or tert-butyl.

In yet other embodiments of any of the above aspects of the invention, $R^3$ is a $C_3$ to $C_{20}$ alkenyl group comprising at least one hydroxyl group or at least one protected hydroxyl group. Moreover, the alkenyl group can further comprise a carbonyl group. For example, in some embodiments of any of the above aspects of the invention, $R^1$ is an alkyl group (for example, a methyl or ethyl group), $R^2$ and $R^4$ are hydrogen, $R^3$ is an alkenyl group comprising at least one hydroxyl group or at least one protected hydroxyl group, the stereochemistry at carbon a is S, and the stereochemistry at carbon b is S.

In various embodiments of any of the above aspects of the invention, the compound can be ebelactone A or ebelactone B.

Additional advantages of the invention will be set forth in part in the description which follows, and in part will be apparent from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

Figure 1:
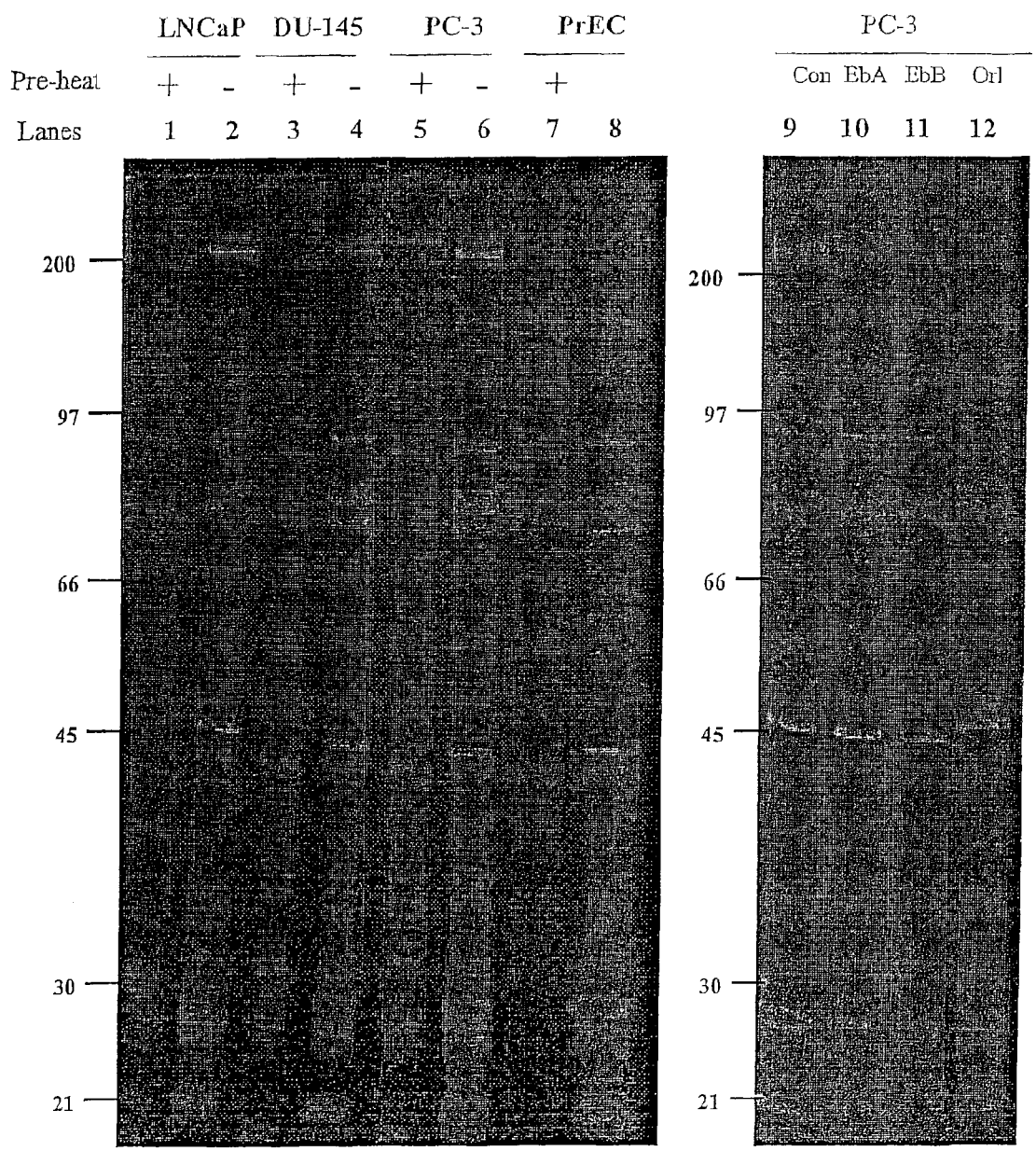
FIG. 1 shows a scan of an SDS-polyacrylamide gel that displays the serine hydrolase activity profile for normal and neoplastic prostate epithelial cells.

The present invention is based on the surprising discovery that beta-lactone compounds can be used to inhibit the activity of fatty acid synthase (FAS), an enzyme known to be up-regulated in tumor cells, and which has been linked to tumor cell proliferation. As shown herein, treatment of tumor cells with beta-lactone compounds induces cell cycle arrest and/or apoptosis, thereby preventing tumor cell proliferation and/or survival.

Described herein are activity-based profiling studies of serine hydrolases, a large gene family encompassing lipases, proteases, and esterases. The objective was to identify serine hydrolases that represent unique points for therapeutic intervention in cancer, using an activity-based profiling assay to screen for small molecule antagonists. In this screening method, the active site of the serine hydrolases is covalently tagged with a probe comprised of fluorophosphonate linked to a reporter (Liu et al. "Activity-based protein profiling: the serine hydrolases." *Proc. Natl. Acad. Sci. U.S.A* 96:14694-9, 1999).

A fluorescently-tagged fluorophosphonate probe (FP-TAMRA) was used to define the profile of serine hydrolases in carcinoma cells, and to identify inhibitors of these enzymes from a small set of beta-lactones. Specifically, three beta-lactones were tested for the ability to block labeling, by FP-TAMRA, of serine hydrolases expressed by mammary carcinoma and prostate carcinoma cells. These beta-lactones included ebelactones A and B, related natural products from actinomycetes (Umezawa et al. "Ebelactone, an inhibitor of esterase, produced by actinomycetes." *J. Antibiot.* (*Tokyo*). 33:1594-1596, 1980; and Uotani et al. "Structural studies on ebelactone A and B, esterase inhibitors produced by actinomycetes." *J. Antibiot.* (*Tokyo*). 35:1495-1499, 1982). Another beta-lactone that was tested was tetrahydrolipstatin, a compound also known as orlistat. Orlistat is a synthetic derivative of the natural product lipstatin, produced by streptomyces. Orlistat is a drug that has been approved by the Food and Drug Administration (FDA) for weight management in obese patients (McNeely and Benfield. "Orlistat." *Drugs* 56:241-9; discussion 250, 1998). Its effectiveness is attributed to its ability to prevent absorption of dietary fat by virtue of its inhibition of pancreatic lipase in the gastrointestinal tract.

All beta-lactones tested inhibited the enzymatic activity of fatty acid synthase (FAS), one of the prominent serine hydrolases identified in our assay. Additional experiments revealed that, surprisingly, orlistat elicits cell cycle arrest in tumor cells at the $G_1$/S boundary, and, in more differentiated tumor cells, apoptosis soon follows. These discoveries reveal a surprising and unappreciated anti-tumor activity for orlistat and other beta-lactone compounds. Accordingly, any beta-lactone, such as (but not limited to) those described herein, can be used in the methods of the invention to treat or prevent tumors that express FAS. Such treatment inhibits tumor cell proliferation and/or induces tumor cell death. Similarly, the methods of the invention can be used to treat or prevent any tumor that overexpresses FAS (e.g., tumors containing cells that express higher levels of FAS than their normal counterparts, e.g., levels that are at least: 10%, 25%, 50%, 75%, 90%, 2-fold, 3-fold, 5-fold or 10-fold higher than their non-tumor cell counterparts).

In its FDA-approved formulation, orlistat is administered orally, and the effects of the drug are largely confined to the gastrointestinal tract, where it inactivates pancreatic lipase. We have found that orlistat blocks fatty acid synthase activity and induces apoptosis in a number of colon cancer cell lines. Accordingly, orlistat can be administered to patients identified as being in need of therapy for the treatment of colon cancer. In addition, orlistat can be administered prophylactically to patients who are identified as being at relatively high risk for developing colon cancer (e.g., a patient who is in remission from colon cancer, a patient whose family has a higher than normal rate of colon cancer, a patient who has one or more genetic mutations that increase the risk of developing colon cancer (e.g., a mutation in the p53 gene), and/or a patient who has or who has had a disease or condition that increases the risk of developing colon cancer); such patients are readily identified by those of skill in the art.

For other tumors (for example, but not limited to, those of the mammary and prostate gland), orlistat can be administered via a different route (e.g., intravenously), or in a different formulation. Those of ordinary skill in the art will readily be able to identify patients who should receive treatment according to the methods of the invention for a cancer, or patients who should receive prophylactic treatment on account of having a higher than normal risk of developing a cancer that can be treated according to the methods of the invention. For example, a patient who is in remission from cancer, a patient whose family has a higher than normal rate of cancer, a patient who has one or more genetic mutations that increase the risk of developing a cancer (e.g., BRCA-1 mutations indicate a higher than normal risk of breast cancer), a patient who has had a laboratory test or medical diagnostic procedure that indicates a higher than normal risk of cancer (e.g., a high level of prostate-specific antigen (PSA) indicates a higher than normal risk for prostate cancer, and the presence of colon polyps, as revealed by colonoscopy, indicates a risk for colon cancer), and/or a patient who has or who has had a disease or condition that increases the risk of developing a cancer (e.g., women who have had breast cancer are in some cases considered by those of skill in the art to have a higher risk of developing endometrial cancer), can be considered as candidates for prophylactic treatment to decrease the likelihood of developing a cancer that could be treated according to the methods of the invention.

The present invention also provides methods based upon a second surprising discovery, i.e., the discovery that FAS is expressed by endothelial cells (the cells that form blood vessels), and is necessary for the proliferation of endothelial cells and for angiogenesis. Angiogenesis, also known as neovascularization, is the process by which endothelial cells infiltrate a tissue, remodel to form blood vessels, and ultimately deliver blood to the tissue. A wide range of physiologic and pathophysiologic processes require angiogenesis, including development, adipogenesis, psoriasis, macular degeneration, and tumor growth and metastasis (see, e.g., Auerbach, W. and Auerbach, R. "Angiogenesis inhibition: a review." *Pharmacol. Ther.* 63:265-311, 1994; Folkman, J. "Angiogenesis in cancer, vascular, rheumatoid and other disease." *Nat. Med.* 1:27-31, 1995; and Creamer, J. D. and Barker, J. N. "Vascular proliferation and angiogenic factors in psoriasis." *Clin. Exp. Dermatol.* 20:6-9, 1995).

The experiments described herein show that FAS is necessary for the proliferation of endothelial cells and for angiogenesis, and that inhibition of FAS activity in endothelial cells inhibits mitogenesis and induces cell cycle arrest. Accordingly, the present invention provides methods for inhibiting angiogenesis and for treating and/or preventing cancers and other diseases that involve pathological angiogenesis, by administering compounds that inhibit FAS activity, thereby inhibiting angiogenesis and treating and/or preventing the disease.

Inhibitors or antagonists of FAS activity can be used in the methods of the invention as anti-angiogenic factors to treat and/or prevent any disease or condition that involves pathological angiogenesis (i.e., angiogenesis that allows a disease or condition to initially develop, to be maintained, or to worsen). Such diseases include, but are not limited to: macular degeneration, diabetic retinopathy, arthritis, obesity, psoriasis, eczema, and scleroderma. In addition, administration of FAS antagonists according to the methods of the invention can be used to treat and/or prevent blood vessel tumors, such as haemangiomas, angiosarcomas, and Kaposi's sarcoma.

Moreover, since tumors cannot grow beyond a volume of 2-3 mm$^3$ without recruiting an additional blood supply, administration of an FAS antagonist to inhibit angiogenesis provides a universal strategy for treating and/or preventing solid tumors that can otherwise exhibit widely different phenotypes. Inhibition of angiogenesis by inhibiting FAS activity can also be used to prevent the metastatic spread of cancer, as infiltration of a tumor by blood vessels provides a route for tumor cells to enter the blood circulation and metastasize.

Examples of tumors that can be treated by administration of a FAS antagonist to inhibit tumor angiogenesis include, but are not limited to: tumors of the brain or nervous system (e.g., neuroblastoma, glioma, and glioblastoma), sarcomas (e.g., osteosarcoma, rhabdomyosarcoma, Ewing's sarcoma, angiosarcoma, Kaposi's sarcoma), lymphoma, and multiple myeloma. Other types of tumors that can be treated by administration of a FAS antagonist (e.g., a beta-lactone) to inhibit tumor angiogenesis include (but are not limited to): leukemias and carcinomas, e.g., carcinomas of the breast, prostate, ovary, endometrium, colon, stomach, liver, pancreas, esophagus, lung, oral mucosa, or skin.

Any beta-lactone, e.g., but not limited to, those examples described herein, can be used in the methods of the invention to inhibit angiogenesis in patients and subjects who would benefit from such inhibition. In addition, any other non-beta-lactone compound that inhibits FAS activity can be used as an anti-angiogenic factor in the methods of the invention. For example, the fungal compound cerulenin and its artificial derivative, c75 (Kuhajda et al. "Synthesis and antitumor activity of an inhibitor of fatty acid synthase." *Proc. Natl. Acad. Sci. U.S.A.* 97:3450-3454, 2000) can be used in the methods of the invention to inhibit FAS activity in order to inhibit angiogenesis and treat any disease or condition that involves pathological angiogenesis.

Beta-Lactone Compounds

The compounds useful in all of the methods of the present invention are generally referred to as beta-lactones. Beta-lactones possess the core structure

where a number of different groups can be substituted for one or more hydrogen atoms of the —CH$_2$CH$_2$— unit present in the ring. For example, beta-lactones useful in the present invention are represented by formula I

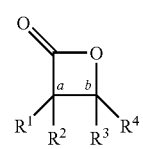

wherein R$^1$, R$^2$, R$^3$, and R$^4$ are, independently, hydrogen, an alkyl group, a cycloalkyl group, a heterocyloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof, and wherein the stereochemistry at carbons a and b is R or S.

Variables such as R$^1$-R$^4$ used throughout the application are the same variables as previously defined unless stated to the contrary.

The term "alkyl group" is defined as a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

The term "alkenyl group" is defined as a hydrocarbon group of 2 to 24 carbon atoms and structural formula containing at least one carbon-carbon double bond.

The term "alkynyl group" is defined as a hydrocarbon group of 2 to 24 carbon atoms and a structural formula containing at least one carbon-carbon triple bond.

The term "halogenated alkyl group" is defined as an alkyl, alkenyl, or alkynyl group as defined above with one or more hydrogen atoms present on these groups substituted with a halogen (F, Cl, Br, I).

The term "aryl group" is defined as any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "cycloalkyl group" is defined as a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorous.

The term "aralkyl" is defined as an aryl group having an alkyl, alkynyl, or alkenyl group as defined above attached to the aromatic group. An example of an aralkyl group is a benzyl group.

The term "hydroxyl group" is represented by the formula —OH. The term "alkoxy group" is represented by the formula —OR, where R can be an alkyl, alkenyl, alkynyl, aryl, aralkyl, cycloalkyl, halogenated alkyl, or heterocycloalkyl group described above.

The term "hydroxyalkyl group" is defined as an alkyl, alkenyl, alkynyl, aryl, aralkyl, cycloalkyl, halogenated alkyl, or heterocycloalkyl group described above that has at least one hydrogen atom substituted with a hydroxyl group. The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

The term "amine group" is represented by the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide group" is represented by the formula —C(O)NRR', where R and R' can be an alkyl, alkenyl, alkynyl, aryl, aralkyl, cycloalkyl, halogenated alkyl, or heterocycloalkyl group described above.

The term "ester" is represented by the formula —OC(O)R, where R can be an alkyl, alkenyl, alkynyl, aryl, aralkyl, cycloalkyl, halogenated alkyl, or heterocycloalkyl group described above.

The term "carbonate group" is represented by the formula —OC(O)OR, where R can be an alkyl, alkenyl, alkynyl, aryl, aralkyl, cycloalkyl, halogenated alkyl, or heterocycloalkyl group described above.

The term "carboxylic acid" is represented by the formula —C(O)OH.

The term "aldehyde" is represented by the formula —C(O)H.

The term "keto group" is represented by the formula —C(O)R, where R is an alkyl, alkenyl, alkynyl, aryl, aralkyl, cycloalkyl, halogenated alkyl, or heterocycloalkyl group described above.

The term "carbonyl group" is represented by the formula C=O.

The term "ether group" is represented by the formula R(O)R', where R and R' can be, independently, an alkyl, alkenyl, alkynyl, aryl, aralkyl, cycloalkyl, halogenated alkyl, or heterocycloalkyl group described above.

The term "halide" is defined as F, Cl, Br, or I.

The term "urethane" is represented by the formula —OC(O)NRR', where R and R' can be, independently, an alkyl, alkenyl, alkynyl, aryl, aralkyl, cycloalkyl, halogenated alkyl, or heterocycloalkyl group described above.

The term "silyl group" is represented by the formula —SiRR'R", where R, R', and R" can be, independently, an alkyl, alkenyl, alkynyl, aryl, aralkyl, cycloalkyl, halogenated alkyl, alkoxy, or heterocycloalkyl group described above. The term "sulfo-oxo group" is represented by the formulas —S(O)$_2$R, —OS(O)$_2$R, or, —OS(O)$_2$OR, where R can be an alkyl, alkenyl, alkynyl, aryl, aralkyl, cycloalkyl, halogenated alkyl, or heterocycloalkyl group described above.

$R^1$-$R^4$ can, independently, possess two or more of the groups listed above. For example, if $R^1$ is a straight chain alkyl group, one of the hydrogen atoms of the alkyl group can be substituted with a hydroxyl group, an alkoxy group, etc. Depending upon the groups that are selected, a first group may be incorporated within second group or, alternatively, the first group may be pendant (i.e., attached) to the second group. For example, with the phrase "an alkyl group comprising an ester group," the ester group may be incorporated within the backbone of alkyl group. Alternatively, the ester can be attached the backbone of the alkyl group. The nature of the group(s) that is (are) selected will determine if the first group is embedded or attached to the second group.

The compounds represented by formula I can be optically active or racemic. The stereochemistry at carbons a and b can vary, and will depend upon the spatial relationship between $R^1$, $R^2$, $R^3$, and $R^4$ to one another. In one embodiment, the stereochemistry at carbons a and b is S. In another embodiment, the stereochemistry at carbons a and b is R. In a further embodiment, the stereochemistry at carbon a is S and the stereochemistry at carbon b is R. In a further embodiment, the stereochemistry at carbons a is R and the stereochemistry at carbon b is S. Using techniques known in the art, it is possible to vary the stereochemistry at carbons a and b.

In one embodiment, $R^1$ is an alkyl group. The alkyl group can be branched or straight chain. In one embodiment, $R^1$ is a straight chain $C_1$ to $C_{20}$, $C_3$ to $C_{18}$, $C_5$ to $C_{16}$, $C_7$ to $C_{14}$, or $C_9$ to $C_{12}$ alkyl group. In another embodiment, $R^1$ is a $C_1$ to $C_5$ alkyl group, such as methyl, ethyl, propyl, isopropyl, butyl, isobutyl, or tert-butyl.

In one embodiment, $R^3$ is a branched or straight chain $C_3$ to $C_{20}$, $C_5$ to $C_{18}$, $C_7$ to $C_{16}$, $C_9$ to $C_{14}$, or $C_{10}$ to $C_{12}$ alkyl group. Alternatively, $R^3$ is a branched or straight chain $C_3$ to $C_{20}$, $C_5$ to $C_{18}$, $C_7$ to $C_{16}$, $C_9$ to $C_{14}$, or $C_{10}$ to $C_{12}$ alkenyl group. The alkyl or alkenyl group of $R^3$ can be substituted with one or more of the following groups: an alkyl group, a cycloalkyl group, a heterocyloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, or a sulfo-oxo group. In a further embodiment, when $R^3$ is an alkyl or alkenyl group, the alkyl or alkenyl group comprises an ester group. The ester can optionally comprise any of the groups listed above. In one embodiment, the ester group further comprises an amide group.

In another embodiment, $R^3$ is a $C_3$ to $C_{20}$ alkenyl group comprising at least one hydroxyl group or at least one protected hydroxyl group. The term "protected hydroxyl group" refers to a hydroxyl group that has been converted to a group such as, but not limited to, an alkoxy group, an ester group, an aldehyde, a keto group, a carbonate, an amide, a silyl group, or a sulfo-oxo group. "*Protecting Groups in Organic Synthesis*" by T. W. Green, John Wiley and Sons, 1981, pp. 10-81, which is incorporated by reference, discloses numerous techniques for protecting a hydroxyl group. In another embodiment, when $R^3$ is an alkenyl group comprising at least one hydroxyl group or at least one protected hydroxyl group, $R^3$ further comprises a carbonyl group.

In one embodiment, $R^1$ is an alkyl group, $R^2$ and $R^4$ are hydrogen, $R^3$ is an alkyl group comprising an ester group, the stereochemistry at carbon a is S, and the stereochemistry at carbon b is S.

In another embodiment, R¹ is an alkyl group, R² and R⁴ are hydrogen, R³ is an alkenyl group comprising an ester group, the stereochemistry at carbon a is S, and the stereochemistry at carbon b is S.

In another embodiment, R¹ is an alkyl group, R² and R⁴ are hydrogen, R³ is an alkenyl group comprising at least one hydroxyl group or at least one protected hydroxyl group, the stereochemistry at carbon a is S, and the stereochemistry at carbon b is S.

In other embodiments, the beta-lactone is a compound provided below, which can be prepared using techniques known in the art:

(1S)-1-[(2S,3S)-3-hexyl-4-oxo-2-oxetanyl]tridecyl ester L-leucine
1-[(3-hexyl-4-oxo-2-oxetanyl)methyl]dodecyl ester L-leucine
3-hexyl-4-(2-hydroxytridecyl)-2-oxetanone
(3S,4S)-3-hexyl-4-[(1S)-1-hydroxytridecyl]-2-oxetanone
1-[(3-hexyl-4-oxo-2-oxetanyl)methyl]dodecyl ester N-[(1,1-dimethylethoxy)carbonyl]-L-leucine
1-[(3-hexyl-4-oxo-2-oxetanyl)methyl]dodecyl ester N-benzoyl-Leucine
3-hexyl-4-(2-hydroxytridecyl)-2-oxetanone
(2S,3R)-4-oxo-3-(4-pentenyl)-2-oxetanecarboxylic acid 1,1-dimethylethyl ester
3-hexyl-4-[2-(3-hydroxypropoxy)tridecyl]-2-oxetanone
4-[2-(3-chloropropoxy)tridecyl]-3-hexyl-2-oxetanone
1-[(3-hexyl-4-oxo-2-oxetanyl)methyl]dodecyl ester N-[4-(hydroxymethyl)benzoyl]-L-Leucine
(2E,4E,7R)-11-[(2R,3R)-3-(hydroxymethyl)-4-oxo-2-oxetanyl]-3,5,7-trimethyl-2,4-undecadienal
(3R,4R)-3-(phenylmethyl)-4-[(trimethylsilyl)ethynyl]-2-oxetanone
(3R,4R)-4-[4-[(4-methoxyphenyl)methoxyl]-1-butynyl]-3-methyl-2-oxetanone
(3R,4R)-3-methyl-4-[3-(phenylmethoxy)-1-propynyl]-2-oxetanone
L-alanyl-3-[(1R,2S)-2-[[[(2R,3S)-3-[(1S)-methylpropyl]-4-oxo-2-oxetanyl]carbonyl]amino]cyclopropyl]-L-alanine
L-alanyl-N5-[[(2R,3S)-3-[(1S)-1-methylpropyl]-4-oxo-2-oxetanyl]carbonyl]-L-ornithine
N-[(1,1-dimethylethoxy)carbonyl]-L-alanyl-3-[(1R,2S)-2-[[[(2R,3S)-3-[(1S)-methylpropyl]-4-oxo-2-oxetanyl]carbonyl]amino]cyclopropyl]-L-alanine
(1S)-1-[[(2S,3S)-3-hexyl-4-oxo-2-oxetanyl]methyl]hexyl ester N-formyl-L-valine
6-[(2-amino-5-chlorobenzoyl)amino]-2,4,6,7-tetradeoxy-2,4,4-trimethyl-,.beta.-lactone, L-ribo-5-Heptulosonic acid
6-[[2-(acetylamino)-5-chlorobenzoyl]amino]-2,4,6,7-tetradeoxy-2,4,4-trimethyl-L-ribo-5-heptulosonic acid beta-lactone
[3S-[3.alpha.,4.beta.(1R*,3E,5S*,7R*,8S*,9S*)]]-4-[8-(acetyloxy)-1,3,5,7,9-pentamethyl-6-oxo-3-undecenyl]-3-methyl-2-oxetanone
[3S-[3.alpha.,4.beta.(1R*,3E,5S*,7R*,8S*,9S*)]]-4-[8-(acetyloxy)-1,3,5,7,9-pentamethyl-6-oxo-3-undecenyl]-3-ethyl-2-oxetanone
4-(8-hydroxy-1,3,5,7,9-pentamethyl-6-oxoundecyl)-3-methyl-2-oxetanone
(3S,4S)-3-hexyl-4-[(2R)-2-hydroxytridecyl1]-2-oxetanone
(3S,4S)-3-hexyl-4-[(2R)-2-[[tris(1-methylethyl)silyl]oxy]tridecyl]-2-oxetanone
(3S,4S)-3-(2-hexenyl)-4-[(2-undecyl-1,3-dioxolan-2-yl)methyl]-2-oxetanone
(3S,4S)-3-(2-hexenyl)-4-(2-oxotridecyl)-2-oxetanone
(4S)-3-3-di-2-hexenyl-4-[(2-undecyl-1,3-dioxolan-2-yl)methyl]-2-oxetanone
L-alanyl-3-[(1R,2S)-2-[[[(2R,3S)-3-[(1S)-1-methylpropyl]-4-oxo-2-oxetanyl]carbonyl]amino]cyclopropyl]-L-alanine
(1S)-1-[[[(2S,3S)-3-hexyl-4-oxo-2-oxetanyl]methyl]dodecyl ester N-[(phenylmethoxy)carbonyl]-L-leucine
(3S,4S)-3-hexyl-4-[(2S)-2-[tetrahydro-2H-pyran-2-yl)oxy]tridecyl]-2-oxetanone
4-nonyl-3-[8-(phenylmethoxy)octyl]-2-oxetanone
3-(8-hydroxyoctyl)-4-nonyl-2-oxetanone
(2E,4E,7R)-11-[(2R,3R)-3-ethenyl-4-oxo-2-oxetanyl]-3,5,7-trimethyl-2,4-Undecadienoic acid diphenylmethyl ester
(2E)-3-[3-[(2R)-6-[(2R,3R)-3-ethenyl-4-oxo-2-oxetanyl]-2-methylhexyl]-3-methyloxiranyl]-2-butenoic acid diphenylmethyl ester
(2E)-3-[3-[(2R)-6-[(2R,3R)-3-(hydroxymethyl)-4-oxo-2-oxetanyl]-2-methylhexyl]-3-methyloxiranyl]-2-butenoic acid diphenylmethyl ester
(2E,4E,7R)-11-[(2R,3R)-3-(hydroxymethyl)-4-oxo-2-oxetanyl]-3,5,7-trimethyl-2,4-undecadienoic acid diphenylmethyl ester
(1S)-1-[[(2S,3S)-3-decyl-4-oxo-2-oxetanyl]methyl]octyl ester N-formyl-glycine
(3S,4S)-4-[(2R)-2-hydroxynonyl]-3-(8-methylnonyl)-3-(trimethylsilyl)-2-oxetanone
(3S,4S)-,3-dodecyl-4-[(2R)-2-hydroxynonyl]-3-(trimethylsilyl)-2-oxetanone
(3R,4S)-3-decyl-4-[(2R)-2-hydroxynonyl]-2-oxetanone
[3S-[3.alpha.,4.beta.(S*)]]-3-decyl-4-(2-hydroxynonyl)-2-oxetanone
(3R,4S)-4-[(2R)-2-[[(1,1-dimethylethyl)dimethylsilyl]oxy]nonyl]-3-(8-methylnonyl)-3-(trimethylsilyl)-2-oxetanone
(3S,4S)-4-[(2R)-2-[[(1,1-dimethylethyl)dimethylsilyl]oxy]nonyl]-3-(8-methylnonyl)-3-(trimethylsilyl)-2-oxetanone
(3R,4S)-4-[(2R)-2-hydroxynonyl]-3-(8-methylnonyl)-3-(trimethylsilyl)-2-oxetanone
(3S,4S)-4-[(2R)-2-hydroxynonyl]-3-(8-methylnonyl)-2-oxetanone
(1S)-1-[[(2S,3S)-3-(8-methylnonyl)-4-oxo-2-oxetanyl]methyl]octyl ester N-(triphenylmethyl)-L-alanine
(3R,4S)-3-decyl-4-[(2R)-2-[[(1,1-dimethylethyl)dimethylsilyl]oxy]nonyl]-3-(trimethylsilyl)-2-oxetanone
(3S,4S)-3-decyl-4-[(2R)-2-[[(1,1-dimethylethyl)dimethylsilyl]oxy]nonyl]-3-(trimethylsilyl)-2-oxetanone
[3S-[3.alpha.,4.beta.(S*)]]-3-decyl-4-(2-hydroxynonyl)-2-oxetanone
[3S-[3.alpha.,4.beta.(S*)]]-3-decyl-4-[2-[[(1,1-dimethylethyl)dimethylsilyl]oxy]nonyl]-2-oxetanone
[3S-[3-.alpha.,4.beta.(S*)]]-3-decyl-4-(2-hydroxynonyl)-2-oxetanone
(3R,4R)-3-methyl-4-(2-phenylethyl)-2-oxetanone
4-heptyl-3,3-dimethyl-2-oxetanone
trans-4-cyclohexyl-3,4-dimethyl-2-oxetanone
[2R-[2.alpha.(2E,4E),3.beta.]]-11-[3-(hydroxymethyl)-4-oxo-2-oxetanyl]-3,5,7-trimethyl-2,4-undecadienoic acid methyl ester
(1S)-1-[[(2S,3S)-3-(8-methylnonyl)-4-oxo-2-oxetanyl]methyl]octyl ester N-formyl-glycine
(1S)-1-[[(2S,3S)-3-decyl-4-oxo-2-oxetanyl]methyl]octyl ester N-formyl-glycine
(1S)-1-[[(2S,3S)-3-decyl-4-oxo-2-oxetanyl]methyl]octyl ester N-formyl-L-alanine
[3R-[3.alpha.4.beta(*)]]-3-[[[(1,1,-dimethylethyl)diphenylsilyl]oxy]methyl]-4-(5-methyl-7-oxooctyl)-2-oxetanone
trans-4-oxo-3-[(triphenylmethoxy)methyl]-2-oxetaneundecanoic acid methyl ester
trans-3-(hydroxymethyl)-4-oxo-2-oxetaneundecanoic acid (2S-trans)-N,N-diethyl-3-hexyl-4-oxo-2-oxetanepentanamide N-formyl-,4-(3-hexyl-4-oxo-2-oxetanyl)butyl ester, (2S-trans)-,L-Leucine (3S-trans)-3-hexyl-4-(4-hydroxybutyl)-2-oxetanone

[2R-[2.alpha.(2E,4E,7R*),3.beta.]]-3,5,7-trimethyl-11-[4-oxo-3-[(triphenylmethoxy)methyl]-2-oxetanyl]-2,4-undecadienoic acid methyl ester

[3.alpha.(E),4.alpha.]-3-(1,3-butadienyl)-3-methyl-4-pentyl-2-oxetanone

[3.alpha.(E),4.beta.]-3-(1,3-butadienyl)-3-methyl-4-pentyl-2-oxetanone

[2R-[2.alpha.(2E,4E,7R*),3.beta]]-11-[3-(methoxymethyl)-4-oxo-2-oxetanyl]-3,5,7-trimethyl-2,4-undecadienoic acid methyl ester

[2R-[2.alpha.(2E,4E),3.beta.]]-11-[3-(hydroxymethyl)-4-oxo-2-oxetanyl]-3,5,7-trimethyl-2,4-undecadienoic acid methyl ester

[3.alpha.,4.beta.(1R*,3E,5S*,7R*,8R*)]-4-[8-[[(1,1-dimethylethyl)dimethylsilyl]oxy]-1,3,5,7-tetramethyl-9-methylene-6-oxo-3-undecenyl]-3-methyl-2-oxetanone

[3.alpha.,4.beta.(1R*,3E,5S*,7R*,8R*)]-4-[8-hydroxy-1,3,5,7-tetramethyl-9-methylene-6-oxo-3-undecenyl]-3-methyl-2-oxetanone

[3.alpha.,4.beta.(1R*,3E,5S*,7R*,8S*,9R*)]-4-[8-hydroxy-1,3,5,7,9-pentamethyl-6-oxo-3-undecenyl)-3-methyl-2-oxetanone 1-[(3-fluoro-3-hexyl-4-oxo-2-oxetanyl)methyl]dodecyl ester N-formyl-L-leucine

[2S-[2.alpha.(R*),3.alpha.]]-1-[(3-fluoro-3-hexyl-4-oxo-2-oxetanyl)methyl]dodecyl ester N-formyl-L-leucine

[3R-[3.alpha.,4.beta.(R*)]]-3-(hydroxymethyl)-4-(5-methyl-7-oxooctyl)-2-oxetanone

[3S-[3.alpha.,4.beta.(2S*,5Z)]]-3-hexyl-4-(2-hydroxy-5-tridecenyl)-2-oxetanone

4-[8-(acetyloxy)octyl]-3-(1-methyl-2-propenyl)-2-oxetanone

In another embodiment, the beta-lactones disclosed in International Publication No. WO 200004300, Japanese Publication No. 03115274, European Publication No. 185359 A2, and U.S. Pat. Nos. 4,931,463, 5,175,186, 5,246,960, 4,873,260, 4,806,564, 4,983,746, 5,260,310, 5,376,674, 5,466,708, and 5,399,720, which are incorporated by reference in their entireties, are useful in the invention.

In one embodiment, the compound having the formula I is tetrahydrolipstatin, which is also referred to as orlistat. The structure of tetrahydrolipstatin is depicted in formula II. In another embodiment, the compound is lipstatin, which is depicted in formula III. The synthesis of tetrahydrolipstatin and lipstatin is disclosed in U.S. Pat. No. 4,598,089, which is incorporated by reference.

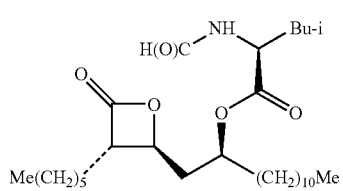

II

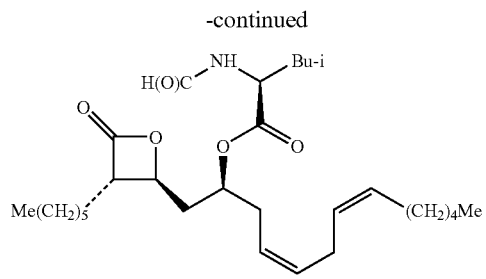

III

In another embodiment, the compound having the formula I is ebelactone A and B, which are depicted in formulas IV and V, respectively. The synthesis of ebelactone A and B is disclosed in the journal article by Paterson and Hulme entitled "Total Synthesis of (−)-Ebelactone A and B" J. Org. Chem., 1995, 60(11), 3288-3300, which is incorporated by reference in its entirety.

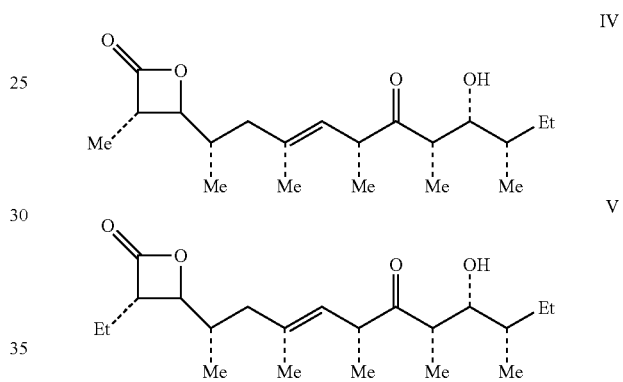

Methods of Administration of Beta-Lactones and Other Inhibitors of Fatty Acid Synthase Activity The FAS antagonists for use in the methods of the invention can be administered to subjects with a pharmaceutically acceptable diluent, carrier, or excipient, in unit dosage form. By "pharmaceutically acceptable" is meant a material that is not biologically or otherwise undesirable, i.e., the material may be administered to an individual along with an FAS antagonist without causing any undesirable biological effects or interacting in a deleterious manner with any of the components of the pharmaceutical composition in which it is contained. Conventional pharmaceutical practice may be employed to provide suitable formulations or compositions to administer such compositions to subjects. Any appropriate route of administration may be employed, for example, but not limited to, intravenous, parenteral, transcutaneous, subcutaneous, intramuscular, intracranial, intraorbital, ophthalmic, intraventricular, intracapsular, intraspinal, intracisternal, intraperitoneal, intranasal, intrarectal, intravaginal, aerosol, or oral administration. Therapeutic formulations may be in the form of liquid solutions or suspensions; for oral administration, formulations may be in the form of tablets or capsules; for intranasal formulations, in the form of powders, nasal drops, or aerosols; for intravaginal formulations, vaginal creams, suppositories, or pessaries; for transdermal formulations, in the form of creams or distributed onto patches to be applied to the skin.

Methods well known in the art for making formulations are found in, for example, Remington: The Science and Practice

*of Pharmacy* (19th ed.) ed. A. R. Gennaro, Mack Publishing Company, Easton, Pa. 1995. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for molecules of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Any beta-lactone or other compound of the invention can be administered singly or in combination. In just example, tetrahydrolipostatin can be administered by itself or in combination with ebelactone A and/or B, and/or in combination with another compound that inhibits FAS.

Dosage

The beta-lactones and other FAS antagonists for use in the methods of the invention may be administered to a subject in an effective amount, i.e., amount sufficient to partially or fully inhibit FAS activity in a subject in need thereof, e.g., to treat a cancer or to inhibit angiogenesis in a subject in need of such treatment. One of ordinary skill in the art will understand that the optimal dosage used will vary according to the individual being treated and the particular cancer, disease, or other condition for which the individual is being treated, the particular compound being used, and the chosen route of administration. The optimal dosage will also vary among individuals on the basis of age, size, weight, gender, and physical condition. Methods for determining optimal dosages are described, for example, in *Remington: The Science and Practice of Pharmacy* (19th ed.) ed. A. R. Gennaro, Mack Publishing Company, Easton, Pa. 1995. Typically, a pharmaceutically effective dosage would be between about 0.001 and 200 mg/kg body weight of the subject to be treated.

Efficacy

The efficacy of administration of a particular dose of a beta-lactone or other FAS antagonist according to the methods of the invention can be determined by evaluating the particular aspects of the medical history, signs, symptoms, and objective laboratory tests that are known to be useful in evaluating the status of a subject in need of inhibition of FAS for the treatment of cancer or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: 1) a subject's physical condition is shown to be improved (e.g., a tumor has partially or fully regressed), 2) the progression of the disease or condition is shown to be stabilized, or slowed, or reversed, or 3) the need for other medications for treating the disease or condition is lessened or obviated, then a particular treatment regimen will be considered efficacious.

Identification of Compounds that Inhibit FAS Activity

In general, compounds that inhibit the activity of FAS (i.e., beta-lactones and other FAS antagonists) can be identified from libraries of natural products or synthetic (or semi-synthetic) extracts or chemical libraries according to methods known in the art and/or described herein. Such screening methods include (but are not limited to): serine hydrolase activity-profiling assays, [$^{14}$C]-acetate incorporation assays, cell proliferation assays, apoptosis assays, and/or angiogenesis assays (see, e.g., Salcedo et al. "Human endothelial cells express CCR2 and respond to MCP-1: direct role of MCP-1 in angiogenesis and tumor progression." *Blood* 96:34, 40, 2000). Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds (e.g., but not limited to, antibodies, peptides, and aptamers). Synthetic compound libraries are commercially available, e.g., from Brandon Associates (Merrimack, N.H.) and Aldrich Chemical (Milwaukee, Wis.).

Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

In sum, a test compound for use in the assay methods of the invention can be any molecule, be it naturally-occurring or artificially-derived, that is surveyed for its ability to: inhibit the activity of fatty acid synthase, inhibit angiogenesis or a disease that involves pathogenic angiogenesis, inhibit cell proliferation, promote apoptosis, and/or promote cell cycle arrest.

Samples for use in the assay methods of the invention include any specimen that can be tested for fatty acid synthase activity and/or that can be used to identify compounds that inhibit fatty acid synthase, inhibit angiogenesis or a disease that involves pathogenic angiogenesis, inhibit cell proliferation, promote apoptosis, and/or promote cell cycle arrest. Examples include, but are not limited to: a sample from a patient or subject, such as a cell, tissue, or tumor sample; a cell (e.g., a prokaryotic or eukaryotic cell that expresses endogenous or recombinant FAS); a lysate (or lysate fraction) or extract derived from a cell; or a molecule derived from a cell or cellular material.

Those skilled in the art of drug discovery and development readily understand that methods for de-replication (e.g., taxonomic de-replication, biological de-replication, and chemical de-replication, or any combination thereof) or the elimination of replicates or repeats of materials already known for their effect on FAS should be employed whenever possible.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract that inhibits FAS activity. The same assays for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using in vitro assays (e.g., for cell cycle arrest, apoptosis, and/or angiogenesis) and in vivo animal models for diseases, conditions, and/or biological processes (e.g., cancer, angiogenesis, or a disease involving pathological angiogenesis) in which it is desirable to inhibit FAS activity to treat or prevent the disease or condition.

EXAMPLES

The present invention is more particularly described in the following examples, which are intended as illustrative only since numerous modifications and variations thereof will be apparent to those of ordinary skill in the art.

Example I

Orlistat and Ebelactones A and B Inhibit Fatty Acid Synthase Activity and Induce Selective Apoptosis of Prostate Tumor Cells Recent work in the area of chemical biology points the way toward direct profiling of protein activity. Two groups have shown it possible to create chemical probes that react at the active site of multiple enzymes of a given class. Liu et al showed how to obtain the profile of serine hydrolase activity with a probe containing fluorophosphonate as the warhead and biotin as the reporter (Liu et al. "Activity-based protein profiling: the serine hydrolase." *Proc. Natl. Acad. Sci. U.S.A* 96:14694-9, 1999). In a related approach, Bogyo's group showed that the family of cysteine proteinases could be tagged covalently with reactive epoxides (Greenbaum et al. "Epoxide electrophiles as activity-dependent cysteine protease profiling and discovery tools" *Chem. Biol.* 7:569-81, 2000). Because activity-based probes bind at the active site of an enzyme, a direct measure of the level of active enzyme can be obtained, and it becomes possible to use straightforward competition assays to screen for inhibitors.

The present study employs such an approach. An activity-based profiling effort was coupled to a simultaneous screen for antagonists of serine hydrolases in prostate cancer cells. This was accomplished with an activity-based probe comprised of a fluorophosphonate warhead linked to the tetramethyl rhodamine fluorophore (FP-TAMRA) (Patricelli et al. "Direct visualization of serine hydrolase activities in complex proteomes using fluorescent active site-directed probes." *Proteomics* 1:1067-1071, 2001).

FIG. 1 is a scan of an SDS-polyacrylamide gel showing an activity profiling experiment for normal and neoplastic prostate epithelial cells. Lysates were generated from primary cultures of normal prostatic epithelial cells (PrEC), and from three prostate tumor cell lines (LNCaP, DU-145, and PC-3). Lysates (40 μg of total protein, at a concentration of 1 mg/ml) were incubated with FP-PEG-TAMRA (2 μM) for one hour at room temperature. Reactions were stopped by the addition of SDS-PAGE loading buffer containing β-mercaptoethanol and boiling. Non-specific labeling with the probe activity was measured in samples that were boiled prior to the addition of fp-PEG-TAMRA (lanes marked +). Samples were resolved by 10% SDS-PAGE and visualized at 605 nm using a Hitachi flat bed gel scanner (lanes 1-8). The effect of three beta-lactones on the activity-labeling of serine hydrolases from PC-3 cells was assessed in a similar manner. Prior to incubation with FP-PEG-TAMRA, lysates (40 μg) were pre-incubated for 30 min with 100 μM of ebelactone A (lane 10), ebelactone B (lane 11), or orlistat (lane 12). Following labeling with FP-PEG-TAMRA the reactions were halted and enzyme activity visualized as described above.

For each cell line tested as described above, approximately fifteen different hydrolases were visualized as fluorescent bands on SDS gels. The pattern of serine hydrolase expression was generally similar among the cell lines, with two significant distinctions. A hydrolase with a mass of approximately 270 kDa was expressed in all of the tumor lines, but was absent in normal PrECs. Peptide mass fingerprinting with mass spectrometry showed this band to be fatty acid synthase (FAS), an observation that was confirmed by immunoprecipitating the complex between FP-TAMRA and FAS.

As the single eukaryotic enzyme capable of synthesizing palmitate, FAS is responsible for generating the precursor for the majority of cellular fatty acids. FAS has a unique structure and mode of action. The enzyme contains six separate enzymatic pockets along with an acyl carrier protein. Palmitate is generated by the enzymes repeated condensation of acetyl co-A and malonyl co-A. Seven such condensation cycles yield the sixteen-carbon polyunsaturated fatty acid palmitate. Palmitate remains covalently attached to the acyl carrier protein of the enzyme until it is liberated by the final enzymatic pocket on the enzyme, the intrinsic thioesterase. This thioesterase is the sole serine hydrolase within FAS, and is targeted by FP-TAMRA.

FAS is known to be up-regulated in a wide range of tumors, and its function has been strongly linked to tumor cell proliferation, making it an attractive therapeutic target for cancer. We capitalized on the fact that FP-TAMRA reacts with the active site of all of the serine hydrolases visualized in FIG. 1 to a selectively identify an inhibitor of the FAS thioesterase domain.

Three beta-lactones, all derivatives of natural products, were tested for the ability to block activity-based labeling of FAS. Interestingly, all three compounds had the ability to inhibit the thioesterase of FAS, but only tetrahydrolipstatin selectively inhibited FAS. Tetrahydroliptstatin, also known as orlistat, is a drug that has already been approved for weight management in obese patients. Interestingly however, the effectiveness of orlistat in this indication is connected to its ability to inhibit pancreatic lipase in the gastrointestinal tract, thereby preventing uptake of dietary fat. Such inhibition occurs following nucleophilic attack by the active site serine on the carbonyl carbon of the lactone ring. The reaction yields a covalent adduct between enzyme and inhibitor (Hadvary et al. "The lipase inhibitor tetrahydrolipstatin binds covalently to the putative active site serine of pancreatic lipase." *J. Biol. Chem.* 266:2021-7, 1991). The inhibition of FAS by orlistat has never been reported, and is not believed to be relevant to its mode of action in weight loss.

Figure 2:
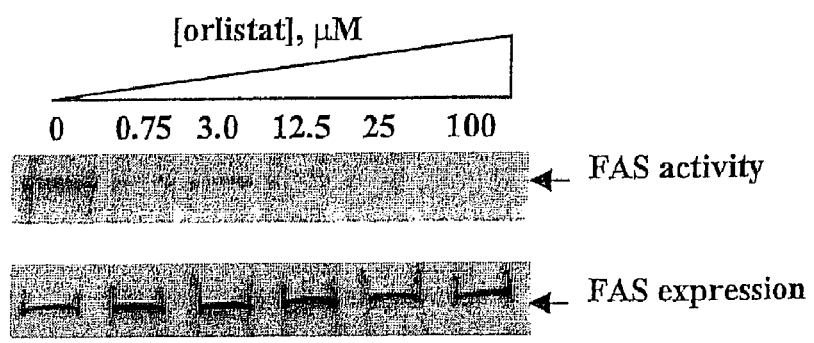
FIG. 2 shows a scan of an SDS-polyacrylamide gel (top panel) that indicates that the labeling of fatty acid synthase (FAS) by FP-Bodipy is inhibited in tetrahydrolipstatin-treated cells, and a scan of a Western blot (bottom panel) that shows that the FAS expression levels are similar in the various samples.

Studies were performed to determine the effect of orlistat on tumor cells. As a first step, we measured the ability to inhibit the activity of FAS in whole cells. PC-3 cells treated with a concentration range of orlistat for one hour were incubated with a membrane-permeable activity-based probe, FP-Bodipy (2 μM), for an additional hour, and the labeled cells were harvested and visualized as described above. A concentration-dependent inhibition of labeling by FP-Bodipy was evident (FIG. 2; top panel), indicating enzyme inhibition. These effects were independent of the abundance of FAS, which was measured from the same treated samples by Western blot (FIG. 2; bottom panel). The effects of orlistat on cellular fatty acid synthesis were measured by assessing the incorporation of [$^{14}$C]-acetate into fatty acids. A level of orlistat capable of inhibiting about 90% of the activity-based labeling of FAS reduced total cellular fatty acid synthesis by approximately 70%.

The effects of orlistat were not limited to inhibition of fatty acid synthesis. This effect apparently has dramatic downstream consequences, because orlistat induced a pronounced apoptotic response in the DU-145 and PC3 cells, which are the two more differentiated prostate lines. A small apoptotic response was observed in the LNCap cells, which are less differentiated and which retain androgen responsiveness. Orlistat has no apoptotic effect on normal prostate epithelial (PrEC) cells, nor on a series of normal human fibroblasts.

Methods

Profiling Serine Hydrolase Activity in Prostate Cell Lines. The LNCaP, DU-145 and PC-3 cell lines (ATCC, Rockville, Md.) were maintained in RPMI 1640 (Irvine Scientific, Santa Ana, Calif.) supplemented with 10% fetal bovine serum at 37° C. in 5% $CO_2$. The PrEC cell line (Clonetics, Walkerville, Md.) was maintained according to the suppliers instructions. Each cell line was maintained in 150-mm tissue culture dishes. To generated protein lysates, cells were washed with ice-cold phosphate buffered saline (PBS) and harvested by scraping with a cell lifter into cold PBS. Cells were collected by centrifugation and the pellets were resuspended in 50 mM Tris-Cl, pH 8.0. Lysis was accomplished by sonication and Dounce-homogenization as described previously (Liu et al., supra; and Kidd et al. "Profiling Serine Hydrolase Activities in Complex Proteomes." *Biochemistry* 40:4005-4015, 2001). The soluble and insoluble cell fractions were separated by ultracentrifugation for one hour at 64,000 rpm at 4° C. Protein concentrations of the soluble fraction was determined by BCA assay (Pierce, Rockford, Ill.) versus a standard concentration of bovine serum albumin (BSA).

The serine hydrolase activity profiles of the prostate cell lines were measured using the fluorophosphonate probe fp-PEG-Tamra using methods described previously (Liu et al., supra; and Kidd et al., supra). Briefly, 40 μl of a 1 mg/ml solution of the soluble fractions of each cell lines were treated with 2 μM fp-PEG-Tamra for one hour at ambient temperature. The labeling reactions were stopped by the addition of Laemmli buffer followed by boiling for 5 minutes. As a control for non-specific reaction of the probe, a duplicate sample was boiled for ten minutes prior to labeling with fp-PEG-Tamra to denature all enzymatic activity. The labeled samples were resolved by 10% SDS-PAGE and visualized by scanning with a Hitachi flatbed scanner at 605 nm.

Alternatively, serine hydrolase activity in whole cells was measured with fp-Bodipy-F1. Cells were plated in 24-well plates and the probe was added to a final concentration of 2 μM and labeled for one hour. The cells were lysed by the addition of Laemmli sample buffer followed by boiling. The labeled samples were resolved by 10% SDS-PAGE and visualized by scanning with a Hitachi flatbed scanner at 505 nm.

Inhibition of Serine Hydrolase Activity with Beta-Lactone Compounds. Ebelactone A and B stocks were made in DMSO. Orlistat was made in EtOH. Cell lysate were generated at 1 mg/ml as described above. Samples (40 μg) were incubated with inhibitors for twenty minutes prior to addition of fp-PEG-TAMRA. The final concentration of DMSO or EtOH in each reaction was 10%. The labeling reactions were stopped by the addition of Laemmli sample buffer and samples were resolved on 10% SDS-PAGE and visualized as described above.

Purification of Serine Hydrolases by Avidin-Biotin Affinity Chromatography. Serine hydrolases were purified from 2.5 mg of soluble cell lysates by avidin-biotin affinity chromatography (Liu et al., supra; and Kidd et al., supra). The lysates were pre-treated with avidin-agarose to remove non-specific binders. Lysates were labeled with fp-PEG-biotin (5 μM) for one hour at room temperature. Protein was separated from unincorporated fp-PEG-biotin by passage over a Nap 25 column. Protein containing fractions were pooled and SDS was added to a concentration of 0.5% and boiled for ten minutes. After boiling the samples were diluted with 50 mM Tris, pH 7.5 and 150 mM NaCl. Avidin-agarose was added to the solution for a one-hour incubation at room temperature. The agarose beads were pelleted by centrifugation and washed eight times with 50 mM Tris, ph 7.5, 150 mM NaCl and 1% Tween 20. Labeled protein was eluted by the addition of Laemmli buffer containing 1% SDS and boiling for ten minutes. Protein was resolved by 10% SDS-PAGE and detected by silver staining. Specific bands were extracted and subjected to in-gel trypsin digests and MALDI-TOF analysis as described previously (Landry et al. "A Method for Application of Samples to Matrix-Assisted Laser Desorption Ionization Time-of-Flight Targets That Enhances Peptide Detection." *Anal. Biochem.* 279:1-8, 2000; Harvey et al. "Insights into a plasma membrane signature." *Physiol. Genomics.* 5:129-136, 2001).

Detection of Fatty Acid Synthase by Western Blot. PC-3 cells ($5 \times 10^4$) were seeded in 24 well plates. Following treatment with orlistat, cells were collected, suspended in Laemmli sample buffer and boiled. Protein was resolved by 10% SDS-PAGE and transferred to nitrocellulose. The membrane was blocked with non-fat milk and probed with an anti-FAS monoclonal antibody (mAb) (Pharmingen, San Diego, Calif.) followed by horseradish peroxidase (HRP)-labeled rabbit anti-mouse IgG (BioRad, Hercules, Calif.) and chemiluminescence detection with Western Lighting Chemiluminescence Reagent (Perkin-Elmer, Boston, Mass.).

Inhibition of Fatty Acid Synthesis by Orlistat. Fatty acid synthesis in cells was measured by [$^{14}$C]-acetate incorporation (Kuhajda et al. "Fatty acid synthesis: a potential selective target for antineoplastic therapy." *Proc. Nat. Acad. Sci. U.S.A.* 91:6379-83, 1994; Pizer et al. "Pharmacological inhibitors of mammalian fatty acid synthase suppress DNA replication and induce apoptosis in tumor cell lines." *Cancer Res.* 58:4611-5, 1998). Cells were seeded at density of $2.5 \times 10^4$ cells/well in 24-well plates. Prior to the addition of orlistat, the wells were washed twice with PBS. Serum-free RPMI containing 300 μg/ml BSA and insulin/transferrin/selenium supplement was added to the wells, with or without orlistat. The cells were incubated for two hours prior to the addition of 1 μCi of [$^{14}$C]-acetate to label newly synthesized fatty acids. After two hours, the labeling medium was removed and the cells were washed with PBS/EDTA and trypsinized. The cells pellets were washed twice more with PBS and fatty acids were extracted by the addition of an equal mixture of chloroform-methanol for 30 minutes. The extracted material was dried under a stream of $N_2$ gas and extracted further with water-saturated butanol. The butanol was removed by drying under a stream of $N_2$ gas and labeled fatty acids were detected by scintillation counting.

Detection of Orlistat-Induced Apoptosis by Annexin V Labeling. Three prostate cancer cell lines (LNCaP, DU-145 and PC-3) and human fibroblasts (HF) were seeded in 35 mm plates. The cells were washed twice with PBS and serum-free medium supplemented with 300 μg/ml BSA (Sigma, St. Louis, Mo.) and insulin/transferrin/selenium cocktail (Life Technologies, Rockville, Md.) containing various concentrations of orlistat was added. At various time points, the cells were harvested by trypsinization and washed twice with PBS. Cells were suspended at $1\times10^6$ cells/ml in annexin V incubation buffer (BioVision, Inc., Mountain View, Calif.) and treated with annexin V-FITC and propidium iodide. Apoptotic cells were quantified by fluorescence-activated cell sorting (FACS) analysis.

Example II

Orlistat Inhibits FAS Activity and Induces Cell Cycle Arrest and Apoptosis in Mammary Carcinoma Cells This study focused on the identification of serine hydrolases active in mammary carcinoma. Activity-based protein profiling was combined with a screen for small molecule antagonists to gain insight into the function of these hydrolases. One of the prominent serine hydrolases, fatty acid synthase, was found to be inhibited by tetrahydrolipstatin, a drug commonly referred to as orlistat. Surprisingly, in mammary carcinoma cells, orlistat elicits cell cycle arrest at the $G_1/S$ boundary. In more differentiated tumor cells, apoptosis soon follows. These experiments show the relevance of fatty acid synthase as a therapeutic target and link fatty acid synthesis to control of common cell cycle checkpoints. The study also reveals an unappreciated anti-tumor activity for orlistat, a drug approved for weight management in obesity.

Methods

Profiling Serine Hydrolase Activity in Mammary Epithelial Cells.

Primary human mammary endothelial cells (HMECs) and MCF-7, MDA-MB-231, and MDA-MB-435 cell lines (ATCC, Rockville, Md.) were maintained in RPMI 1640 (Irvine Scientific, Santa Ana, Calif.) supplemented with 10% fetal bovine serum at 37° C. in 5% $CO_2$. Each cell line was maintained in 150-mm tissue culture dishes. To generated protein lysates, cells were washed with ice-cold phosphate buffered saline (PBS) and harvested by scraping with a cell lifter into cold PBS. Cells were collected by centrifugation and the pellets were resuspended in 50 mM Tris-Cl, pH 8.0. Lysis was accomplished by sonication and Dounce homogenization as described previously (Liu et al. "Activity-based protein profiling: the serine hydrolase." *Proc. Natl. Acad. Sci. U.S.A* 96:14694-9, 1999; Kidd et al. "Profiling Serine Hydrolase Activities in Complex Proteomes." *Biochemistry* 40:4005-4015, 2001). The soluble and insoluble cell fractions were separated by ultracentrifugation for one hour at 64,000 rpm at 4° C. Protein concentrations of the soluble fraction was determined by BCA assay (Pierce, Rockford, Ill.) versus a standard concentration of bovine serum albumin (BSA).

The serine hydrolase activity profiles of the prostate cell lines were measured using the fluorophosphonate probe fp-PEG-TAMRA using methods described previously (Liu et al., supra; Kidd et al., supra). Briefly, 40 μl of a 1 mg/ml solution of the soluble fractions of each cell lines were treated with 2 μM fp-PEG-TAMRA for one hour at ambient temperature. The labeling reactions were stopped by the addition of Laemmli buffer followed by boiling for 5 minutes. As a control for non-specific reaction of the probe, a duplicate sample was boiled for ten minutes prior to labeling with fp-PEG-TAMRA to denature all enzymatic activity. The labeled samples were resolved by 10% SDS-PAGE and visualized by scanning with a Hitachi flatbed scanner at 605 nm.

Alternatively, serine hydrolase activity in whole cells was measured with fp-Bodipy-F1. Cells were plated in 24-well plates and the probe was added to a final concentration of 2 μM and labeled for one hour. The cells were lysed by the addition of Laemmli sample buffer followed by boiling. The labeled samples were resolved by 10% SDS-PAGE and visualized by scanning with a Hitachi flatbed scanner at 605 nm.

Inhibition of Serine Hydrolase Activity with Beta-Lactone Compounds.

Ebelactone A and B stocks were made in DMSO. Orlistat was made in EtOH. Cell lysate were generated at 1 mg/ml as described above. Samples (40 μg) were incubated with inhibitors for twenty minutes prior to addition of fp-PEG-TAMRA. The final concentration of DMSO or EtOH in each reaction was 10%. The labeling reactions were stopped by the addition of Laemmli sample buffer and samples were resolved on 10% SDS-PAGE and visualized.

Purification of Serine Hydrolases by Avidin-Biotin Affinity Chromatography.

Serine hydrolases were purified from 2.5 mg of soluble cell lysates by avidin-biotin affinity chromatography (Liu et al., supra; Kidd et al., supra). The lysates were pre-treated with avidin-agarose to remove non-specific binders. Lysates were labeled with fp-PEG-biotin (5 μM) for one hour at room temperature. Protein was separated from unincorporated fp-PEG-biotin by passage over a Nap 25 column. Protein containing fractions were pooled and SDS was added to a concentration of 0.5% and boiled for ten minutes. After boiling the samples were diluted with 50 mM Tris, pH 7.5 and 150 mM NaCl. Avidin-agarose was added to the solution for a one-hour incubation at room temperature. The agarose beads were pelleted by centrifugation and washed eight times with 50 mM Tris, ph 7.5, 150 mM NaCl and 1% Tween 20. Labeled protein was eluted by the addition of Laemmli buffer containing 1% SDS and boiling for ten minutes. Protein was resolved by 10% SDS-PAGE and detected by silver staining. Specific bands were extracted and subjected to in-gel trypsin digests and MALDI-TOF analysis as described previously (Landry et al. "A Method for Application of Samples to Matrix-Assisted Laser Desorption Ionization Time-of-Flight Targets That Enhances Peptide Detection." *Anal. Biochem.* 279:1-8, 2000; Harvey et al. "Insights into a plasma membrane signature." *Physiol. Genomics.* 5:129-136, 2001).

Detection of Fatty Acid Synthase by Western Blot.

MDA-MB-435 cells ($5\times10^4$) were seeded in 24 well plates. Following treatment with orlistat, cells were collected, suspended in Laemmli sample buffer and boiled. Protein was resolved by 10% SDS-PAGE and transferred to nitrocellulose. The membrane was blocked with non-fat milk and probed with an anti-FAS mAb (Pharmingen, San Diego, Calif.) followed by HRP-labeled rabbit anti-mouse IgG (Bio-Rad, Hercules, Calif.) and chemiluminescence detection with Western Lighting Chemiluminescence Reagent (Perkin-Elmer, Boston, Mass.).

Inhibition of Fatty Acid Synthesis by Orlistat.

Fatty acid synthesis in cells was measured by [$^{14}$C]-acetate incorporation (Kuhajda et al. "Fatty acid synthesis: a potential selective target for antineoplastic therapy." *Proc. Nat. Acad. Sci. U.S.A.* 91:6379-83, 1994; Pizer et al. "Pharmacological inhibitors of mammalian fatty acid synthase suppress DNA replication and induce apoptosis in tumor cell lines." *Cancer Res.* 58:4611-5, 1998). Cells were seeded at density of $2.5\times10^4$ cells/well in 24-well plates. Prior to the addition of orlistat, the wells were washed twice with PBS. Serum-free RPMI containing 300 μg/ml BSA and insulin/transferrin/selenium supplement was added to the wells, with or without orlistat. The cells were incubated for two hours prior to the addition of 1 μCi of [$^{14}$C]-acetate to label newly synthesized fatty acids. After two hours, the labeling medium was removed and the cells were washed with PBS/EDTA and trypsinized. The cells pellets were washed twice more with PBS and fatty acids were extracted by the addition of an equal mixture of chloroform-methanol for 30 minutes. The extracted material was dried under a stream of $N_2$ gas and extracted further with water-saturated butanol. The butanol was removed by drying under a stream of $N_2$ gas and labeled fatty acids were detected by scintillation counting.

Detection of Orlistat-Induced Apoptosis.

Three breast cancer cell lines (MDA-MB-435, MDA-MB-231, and MCF-7) and human mammary epithelial cells (HMEC) were seeded in 96-well plates at $1\times10^4$ cells per well. The cells were washed twice with PBS and then incubated in serum free medium supplemented with 300 µg/ml BSA (Sigma) and insulin/transferrin/selenium cocktail (Life Technologies, Rockville, Md.) containing the indicated concentrations of orlistat. After twenty-four hours, the media was removed and the Cell Death Detection ELISA$^{plus}$ kit (Roche, Indianapolis, Ind.) was used to measure DNA fragmentation. The raw data were transformed to % cell death based on positive control standards.

Results

The Serine Hydrolase Profile of Mammary Carcinoma.

Figure 3:
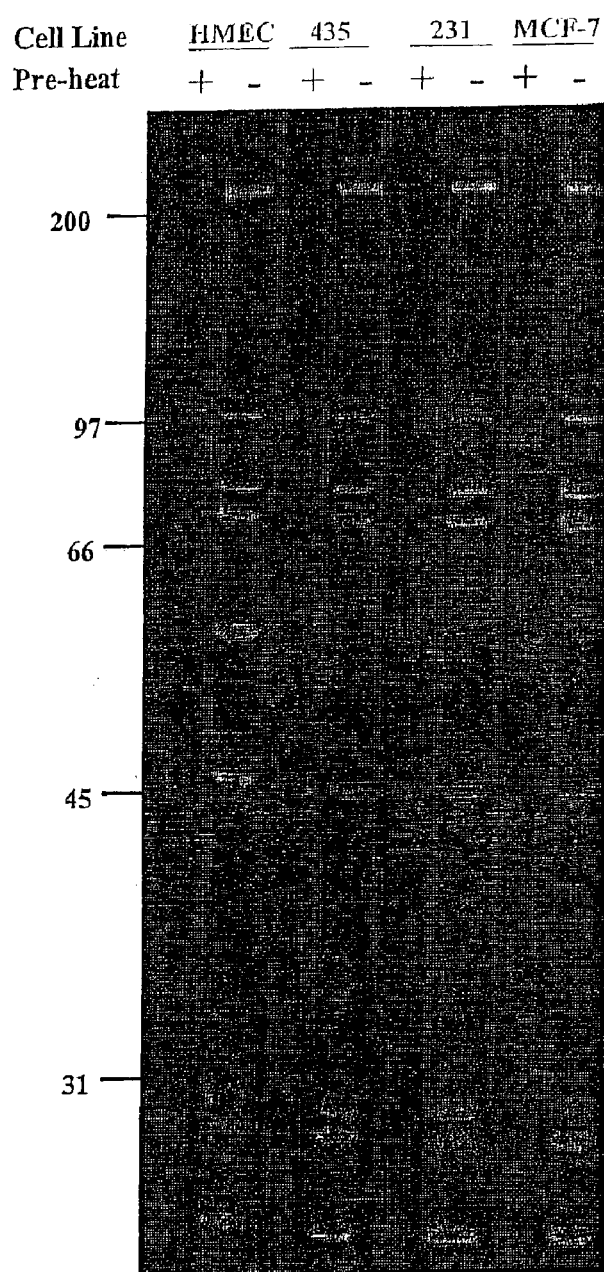
FIG. 3 shows a scan of an SDS-polyacrylamide gel that displays the serine hydrolase profile of normal and neoplastic mammary epithelial cells.

An activity-based probe was used to define the serine hydrolase profile of breast cancer cell lines. The probe is comprised of a fluorophosphonate warhead linked to the TAMRA fluorophore (FP-TAMRA) (Patricelli et al. "Direct visualization of serine hydrolase activities in complex proteomes using fluorescent active site-directed probes." *Proteomics* 1:1067-1071, 2001). Primary cultures of normal mammary epithelial cells (HMEC) were compared to three breast cancer cell lines, MCF-7, MDA-MB-231 and MDA-MB-435. These three lines represent a spectrum of phenotypes (Kurebayashi et al. "Quantitative demonstration of spontaneous metastasis of MCF-7 human breast cancer cells co-transfected with fibroblast growth factor 4 and LacZ." *Cancer Res.* 53:2178-2187, 1993; Shafie et al. "Formation of metastasis by human breast carcinoma cells (MCF-7) in nude mice." *Cancer Lett.* 11:81-87, 1980; and Price et al. "Tumorigenicity and metastasis of human breast carcinoma cell lines in nude mice." *Cancer Res.* 50:717-721, 1990). MCF-7 cells are estrogen responsive and non-invasive. The other two lines have lost estrogen control and are invasive in animals. Lysates from each cell type were reacted with FP-TAMRA and then resolved on SDS-PAGE (FIG. 3). In each case approximately fifteen different active hydrolases are visualized as fluorescent bands on SDS gels. The pattern of serine hydrolase expression is generally similar among the cell lines.

Screening for Serine Hydrolase Inhibitors.

We capitalized on the fact that FP-TAMRA reacts at the active site of all of the serine hydrolases visualized in FIG. 3, by performing a simultaneous screen for antagonists of all of these enzymes. Three beta-lactones were tested for the ability to block labeling of the mammary serine hydrolases by FP-TAMRA: ebelactones A and B, and orlistat.

Figure 4:
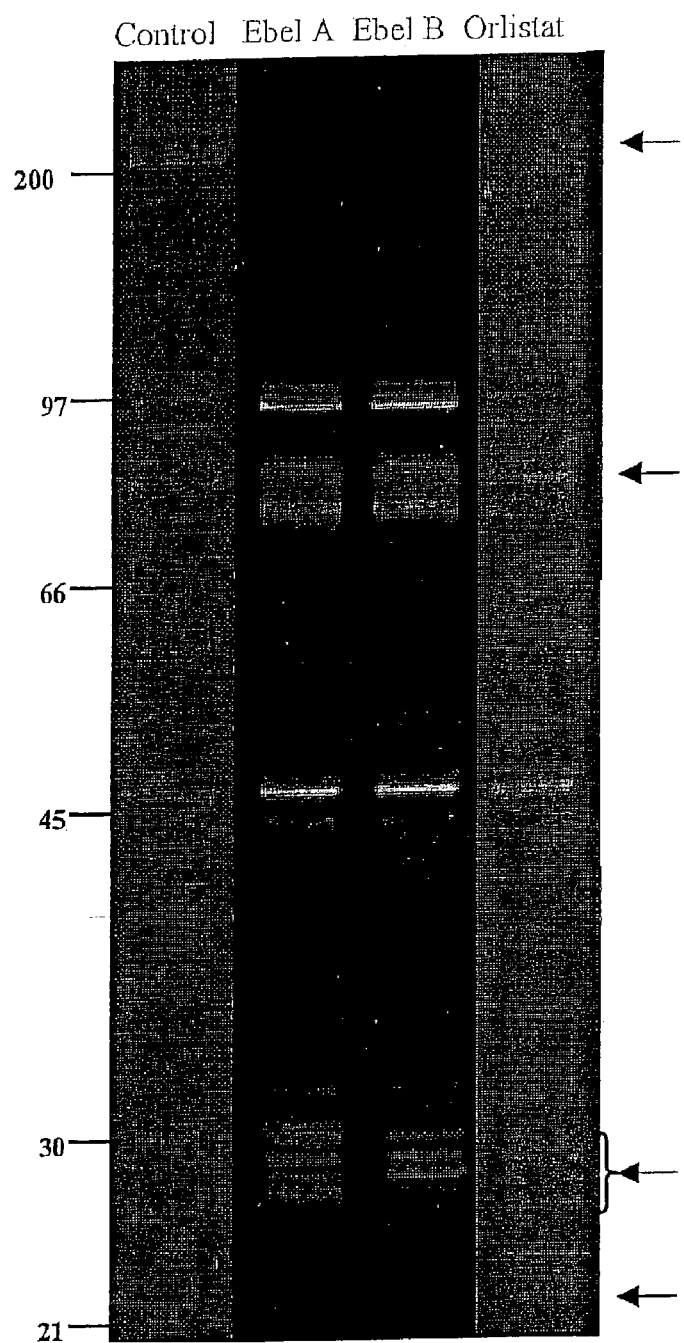
FIG. 4 shows a scan of an SDS-polyacrylamide gel from an experiment in which beta-lactones were screened for their ability to inhibit the activity of serine hydrolases.

Labeling of serine hydrolases in the cell lysates with FP-TAMRA was challenged with each of the beta-lactones. Inhibition experiments were performed under pre-steady state conditions, so that relative $IC_{50}$ values could be compared. All three compounds blocked labeling of hydrolases by FP-TAMRA (FIG. 4), indicating inhibition at the active site serine. Interestingly though, each compound exhibited a different spectrum of inhibition. For example, ebelactone A was a potent inhibitor of the hydrolase expressed at 28 kDa, but ebelactone B had little effect on this enzyme. Conversely, ebelactone B abolished labeling of a hydrolase migrating at 31 kDa, but the same concentration of ebelactone A was far less effective. Tetrahydrolipstatin is selective for the hydrolase at 270 kDa that is expressed in breast cancer cell lines.

To identify the hydrolases that are inhibited by each beta-lactone, a slightly different labeling strategy was used. Cell lysates were reacted with a biotinylated derivative of fluorophosphonate (Liu et al., supra). Then, the tagged hydrolases were subjected to affinity purification on avidin-agarose columns. Bands in the eluate corresponding to hydrolases hit by the beta-lactones were excised and subjected to peptide mass fingerprinting by MALDI-TOF mass spectrometry. In some instances the identification was confirmed by MS/MS sequencing. The 270 kDa band that is inhibited exclusively by orlistat was found to be fatty acid synthase (FAS). The identity of the protein was confirmed by immunoprecipitating the complex between FP-TAMRA and FAS with an anti-FAS monoclonal antibody.

Orlistat Inhibits FAS in Whole Cells and Blocks Cellular Fatty Acid Synthesis.

Studies were performed to determine whether orlistat could block the biological function of FAS in whole cells. MDA-MB-435 cells treated with a range of orlistat were probed with a membrane-permeable activity probe, FP-Bodipy. A concentration-dependent inhibition of the labeling of cellular FAS by orlistat was evident. These effects were independent of the abundance of FAS, which was measured from the same treated samples by Western blot. We measured the effects of orlistat on cellular fatty acid synthesis. MDA-MB-435 cells were fed [$^{14}$C]-acetate as a precursor, and treated with orlistat. At 100 µm orlistat the incorporation of [$^{14}$C]-acetate into cellular fatty acids was reduced by approximately 70%. This observation is taken to indicate that the biological activity of FAS in tumor cells is drastically reduced by orlistat.

Induction of Tumor Cell Apoptosis by Orlistat.

The effect of orlistat on apoptosis in the MDA-MB-435, MDA-MB-231 or MCF-7 mammary carcinoma cell lines, or in primary cultures of normal mammary epithelial cells or fibroblasts (HF cells; ATCC, Rockville, Md.), was measured using DNA fragmentation as an indicator. Cells ($1\times10^4$/well) were treated with orlistat in defined medium for 48 hours. Cells were lysed and DNA fragmentation was measured by ELISA and normalized to apoptosis induced by camptothecin. In each case triplicate measurements were made with a standard deviation of less then 10%.

Figure 5:
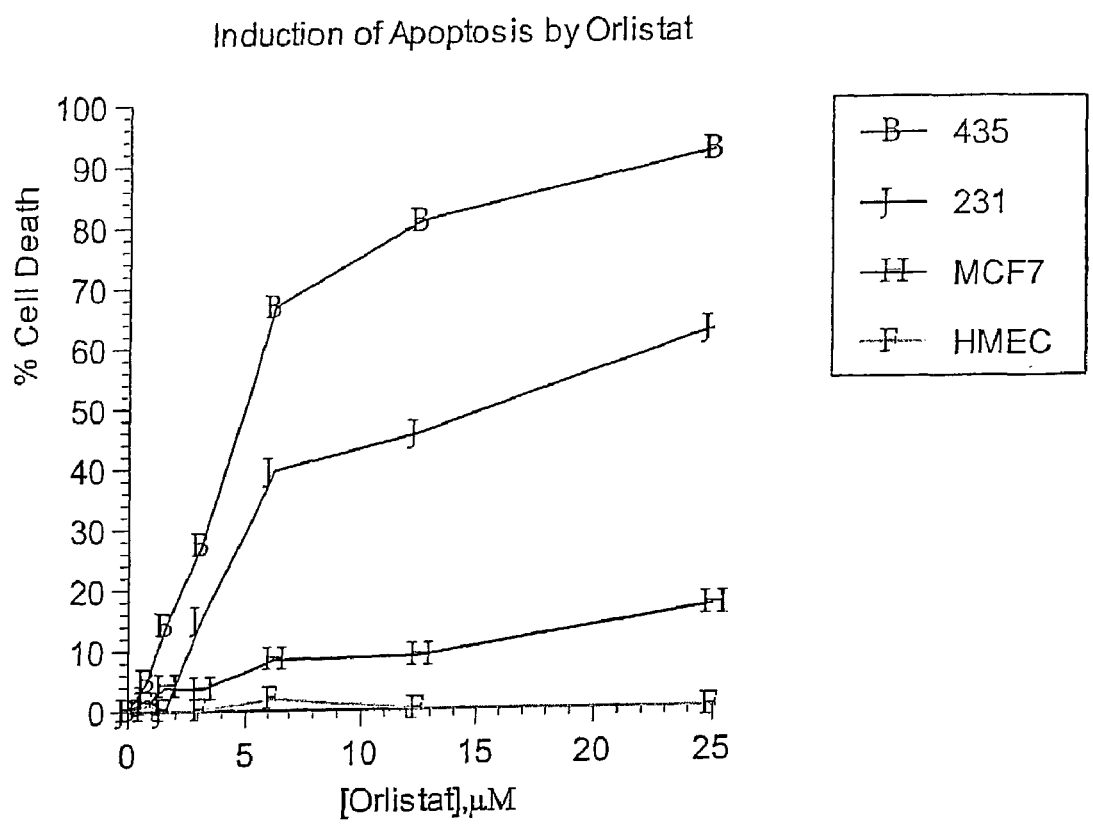
FIG. 5 is a graph showing the effect of orlistat on apoptosis of normal and neoplastic mammary epithelial cells.

Interestingly, orlistat induced an apoptotic response in all three tumor lines, without effect on normal HMECs (FIG. 5) nor on fibroblasts. The apoptotic response was most pronounced in the more differentiated tumor lines, MDA-MB-435 and MDA-MB-231. Orlistat had only a moderate effect on the MCF-7 cells. This analysis was extended by comparing the effect of orlistat on MDA-MB-435 cells and the HMECs across a range of orlistat. Half-maximal response in the MDA-MB-435 cells was observed at about 4 µM orlistat. No effect was evident in the HMECs.

Orlistat Induces $G_1$/S Cell Cycle Arrest.

Figure 6:
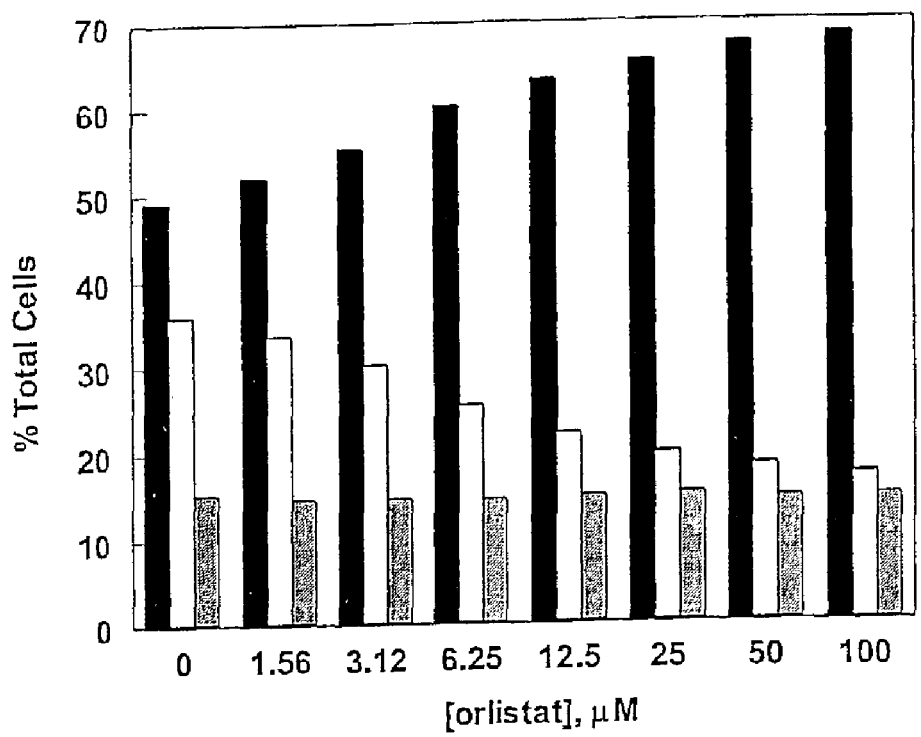
FIG. 6 is a graph showing the induction of cell cycle arrest in mammary carcinoma cells by orlistat.

To determine if the apoptotic effects of orlistat are associated with a cell cycle checkpoint, the effect of orlistat on cell cycle progression of the MDA-MB-435 cells was measured by staining cellular DNA with propidium iodide, and then assessing DNA content by flow cytometry. Treatment with orlistat caused a pronounced increase in the percentage of cells present in $G_1$, and a corresponding decrease in the percent of cells in S phase (FIG. 6: $G_1$=dark bars, S=open bars, and $G_2$/M=grey bars). These observations link the inhibition of FAS by orlistat to the Rb axis that controls $G_1$/S progression.

Example III

Orlistat Inhibits Endothelial Cell Proliferation and FAS Activity

The experiments described below provide the first demonstration that human endothelial cells express FAS, and show that inhibition of FAS with orlistat induces a $G_1$ cell cycle block and inhibits endothelial proliferation.

Results

Orlistat Inhibits the Serine Hydrolase Activity of HUVEC Fatty Acid Synthase.

An activity-based probe, composed of a fluorophosphonate reactive group linked to the Tamra fluorophore (fp-TAMRA), was used to define the serine hydrolase profile of human umbilical vein endothelial cells (HUVEC). A cell lysate was allowed to react with fp-TAMRA and the proteins resolved by SDS-PAGE. Approximately 19 different hydrolases were detected as fluorescent bands on the gel. An intense band identified as fatty acid synthase (FAS) was evident close to the 220 kDa molecular weight marker.

Orlistat was assessed as an inhibitor of endothelial serine hydrolases by pre-incubating cell lysates with orlistat in a range of concentrations. FAS was the only hydrolase affected, showing a selective reduction in subsequent binding of fp-TAMRA. Orlistat inhibited FAS activity by a maximum of 80%, and orlistat concentrations of 5-10 μM were required to reach this level of inhibition. The half maximal effect was accomplished by 660 nM orlistat.

Orlistat Inhibits Proliferation of HUVECs.

The effect of orlistat on HUVEC proliferation induced by several mitogenic stimuli was assessed by BrdU incorporation. Orlistat and mitogen were added simultaneously to serum-starved cells, and BrdU included during the period equivalent to the second round of the cell cycle after mitogen addition. Orlistat inhibited proliferation induced by complete endothelial medium (containing a undefined mixture of mitogens), by bFGF and by VEGF. The minimal amount of proliferation occurring in basal medium supplemented with 0.2% fetal calf serum (FCS) only was also inhibited. Maximum inhibition was almost 90% for cells stimulated with complete medium or bFGF, but nearer to 80% when VEGF was used, and was achieved at orlistat concentrations of 10 μM and above. Orlistat concentrations required for a half maximal effect were 4 μM, 1 μM and 1.25 μM respectively.

Orlistat Induces G1 Cell Cycle Arrest.

Progression of HUVEC through the cell cycle was monitored by flow cytometric assessment of DNA content. After 24 h serum starvation, few cells were undergoing cell division; the distribution of cells between G1, S and G2/M phases was 67%, 6% and 27%, respectively. In the absence of orlistat, cells re-exposed to Endothelial Growth Medium entered S phase 12 h later, with DNA synthesis reaching a population maximum at 16 h. The percentage of cells in G2/M peaked 4 h later, at 20 h, after which the cells rapidly re-entered S phase. In the presence of 10 μM orlistat, entry into the first round of S phase was partially blocked, with a corresponding increase in the percentage of cells remaining in G1, and decrease in cells progressing on to G2/M phase. The second S phase peak was completely inhibited by orlistat, with the cells remaining in G1. These observations indicate that orlistat induces a G1 cell cycle block in HUVECs.

Methods

Effect of Orlistat on FAS Activity in HUVEC Lysates.

HUVEC lysates (40 μg) were preincubated for 30 min with orlistat at concentrations ranging from 10-0 μM, followed by a one hour incubation with fp-TAMRA to tag any remaining active sites. Non-specific labeling with the probe was determined by boiling samples prior to the addition of fp-Tamra. Reactions were stopped by addition of SDS loading buffer, followed by boiling. Proteins (30 μg/lane) were resolved by SDS-PAGE using a 10% gel, and visualized at 605 nm using a Hitachi flat bed gel scanner. The density of the band corresponding to FAS was measured using Image Analysis v2.0 software (Hitachi Genetic Systems) and the effect of orlistat on FAS activity was expressed as a percentage of the band intensity in the untreated lysate.

Effect of Orlistat on Endothelial Cell Proliferation.

Cell proliferation was measured by incorporation of BrdU. HUVEC were seeded in 96 well plates at a density of 2000 cells/well and cultured in Endothelial Growth medium (EGM; Clonetics, Walkerville, Md.) for 24 h at 37° C. Cells were serum-starved for further 24 h in Endothelial Basal Medium (EBM; Clonetics, Walkerville, Md.)+0.2% FCS. Medium was replaced with orlistat (40-0 μM) diluted in (A) EGM, (B) EBM+2% FCS+bFGF (5 ng/ml), (C) EBM+2% FCS+VEGF (20 ng/ml) or (D) EBM+0.2% FCS. Cells were incubated 48 h at 37 deg C., with BrdU present during the final 24 h. Medium was removed, the cell monolayers fixed, and BrdU incorporation measured by ELISA. Proliferation was expressed as a percentage of that measured in the absence of orlistat.

Effect of Orlistat on HUVEC Passage Through the Cell Cycle.

HUVEC were seeded into 6-well plates at a density of 74,000 cells/well and cultured in EGM for 24 h at 37 deg C. Cells were serum-starved for further 24 h in EBM+0.2% FCS. Medium was replaced with EGM+/−10 μM orlistat, and cells cultured for up to 38 h more. Untreated and orlistat-treated cells were sampled at 4 h intervals. The DNA content of cells was assessed by binding of propidium iodide, and percentage of cells in (A) G1 phase, (B) S phase and (C) G2/M phase at each time point was calculated.

INCORPORATION BY REFERENCE

Throughout this application, various publications, patents, and/or patent applications are referenced in order to more fully describe the state of the art to which this invention pertains. The disclosures of these publications, patents, and/or patent applications are herein incorporated by reference in their entireties, and for the subject matter for which they are specifically referenced in the same or a prior sentence, to the same extent as if each independent publication, patent, and/or patent application was specifically and individually indicated to be incorporated by reference.

Other Embodiments

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of identifying a beta-lactone that inhibits tumor cell proliferation, comprising:
   a) contacting a sample comprising tumor cells with a beta-lactone, wherein the beta-lactone has the formula I:

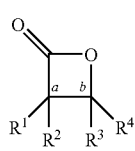

wherein $R^1$, $R^2$, $R^3$, and $R^4$ are, independently, hydrogen, an alkyl group, a cycloalkyl group, a heterocyloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, or a sulfo-oxo group, and wherein the stereochemistry at carbons a and b is R or S; and
   b) measuring the amount of cell proliferation, cell cycle progression, cell cycle arrest, or apoptosis in the sample exposed to the beta-lactone,
   whereby a decrease in cell proliferation, a decrease in cell cycle progression, an increase in cell cycle arrest, or an increase in apoptosis in the sample comprising tumor cells exposed to the beta-lactone, relative to the amount of proliferation, cell cycle progression, cell cycle arrest, or apoptosis in a sample comprising tumor cells not contacted with the beta-lactone, identifies a beta-lactone that inhibits proliferation of a tumor cell.

2. The method of claim 1 wherein $R^1$ is a straight alkyl group.

3. A method of identifying a beta-lactone that inhibits angiogenesis, comprising:
   a) contacting a sample comprising endothelial cells with a beta-lactone having the formula I:

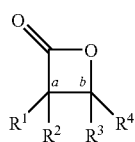

wherein $R^1$, $R^2$, $R^3$, and $R^4$ are, independently, hydrogen, an alkyl group, a cycloalkyl group, a heterocyloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, or a sulfo-oxo group, and wherein the stereochemistry at carbons a and b is R or S; and
   b) measuring the amount of endothelial cell proliferation, cell cycle progression, or cell cycle arrest in the sample, whereby a decrease in cell proliferation, a decrease in cell cycle progression, or an increase in cell cycle arrest in the sample, relative to the amount of cell proliferation, cell cycle progression, or cell cycle arrest in a sample comprising endothelial cells not contacted with the beta-lactone, identifies a beta-lactone that inhibits angiogenesis.

4. The method of claim 3 wherein $R^1$ is a straight alkyl group.

5. A method of identifying a beta-lactone that inhibits angiogenesis, comprising:
   a) contacting a sample with a beta-lactone, wherein the sample comprises angiogenic cells and wherein the beta-lactone has the formula I:

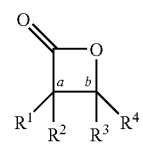

wherein $R^1$, $R^2$, $R^3$, and $R^4$ are, independently, hydrogen, an alkyl group, a cycloalkyl group, a heterocyloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, or a sulfo-oxo group, and wherein the stereochemistry at carbons a and b is R or S, and
   b) measuring the amount of angiogenesis in the sample, whereby a decrease in the amount of angiogenesis in the sample, relative to the amount of angiogenesis in a sample not contacted with the beta-lactone, identifies a beta-lactone that inhibits angiogenesis.

6. The method of claim 5 wherein $R^1$ is a straight alkyl group.

* * * * *